(12) United States Patent
Jagger et al.

(10) Patent No.: US 7,766,010 B2
(45) Date of Patent: Aug. 3, 2010

(54) METHOD OF CONTROLLING THE RATE OF OXYGEN PRODUCED BY AN OXYGEN CONCENTRATOR

(75) Inventors: Theodore W. Jagger, White Bear Lake, MN (US); Nicholas P. Van Brunt, White Bear Lake, MN (US); John A. Kivisto, Oak Grove, MN (US); Perry B. Lonnes, White Bear Lake, MN (US)

(73) Assignee: VBOX, Incorporated, White Bear Lake, MN (US)

( * ) Notice: Subject to any disclaimer, the term of this patent is extended or adjusted under 35 U.S.C. 154(b) by 220 days.

(21) Appl. No.: 11/054,342

(22) Filed: Feb. 9, 2005

(65) Prior Publication Data

US 2006/0174882 A1 Aug. 10, 2006

(51) Int. Cl.
- *A61M 15/06* (2006.01)
- *B01D 59/26* (2006.01)
- *B01D 19/00* (2006.01)

(52) U.S. Cl. .......... 128/202.21; 95/96; 95/97; 95/98; 95/99; 95/100; 95/101; 95/102; 95/103; 96/121; 96/130; 96/133; 96/157

(58) Field of Classification Search .......... 96/121, 96/130, 133, 157; 95/96–103; 128/202.21
See application file for complete search history.

(56) References Cited

U.S. PATENT DOCUMENTS

| | | | |
|---|---|---|---|
| 4,194,890 A * | 3/1980 | McCombs et al. ......... | 95/23 |
| 4,449,990 A * | 5/1984 | Tedford, Jr. ............... | 95/26 |
| 4,472,177 A * | 9/1984 | Sircar ...................... | 95/11 |
| 4,491,459 A | 1/1985 | Pinkerton | |
| 4,648,888 A | 3/1987 | Rowland | |
| 4,813,977 A | 3/1989 | Schmidt et al. | |
| 4,826,510 A | 5/1989 | McCombs | |
| 4,925,464 A | 5/1990 | Rabenau et al. | |
| 4,971,609 A * | 11/1990 | Pawlos ..................... | 96/128 |
| 5,084,075 A | 1/1992 | Sircar et al. | |
| 5,114,440 A * | 5/1992 | Reiss ........................ | 95/96 |

(Continued)

FOREIGN PATENT DOCUMENTS

EP 0 860 646 A2 2/1998

(Continued)

OTHER PUBLICATIONS

Recommendations of the Fifth Oxygen Consensus Conference, 1999.

(Continued)

*Primary Examiner*—Loan H Thanh
*Assistant Examiner*—Nihir Patel
(74) *Attorney, Agent, or Firm*—Kinney & Lange, P.A.

(57) ABSTRACT

A method of providing concentrated oxygen product gas to a patient. The method comprises producing product gas by a vacuum swing adsorption (VSA) process with an oxygen concentrator comprising a plurality of separation columns connected to a vacuum source driven by a motor. Separated product gas is then pumped to a product reservoir. The pressure of the reservoir is monitored and used to adjust the speed of the motor based on the reservoir pressure. The separated gas is then delivered to the patient.

21 Claims, 19 Drawing Sheets

U.S. PATENT DOCUMENTS

| | | | |
|---|---|---|---|
| 5,366,541 A | 11/1994 | Hill et al. | |
| 5,429,666 A | 7/1995 | Agrawal et al. | |
| RE35,099 E | 11/1995 | Hill | |
| 5,531,807 A | 7/1996 | McCombs | |
| 5,593,478 A | 1/1997 | Hill et al. | |
| 5,656,066 A | 8/1997 | Reiss et al. | |
| 5,730,778 A | 3/1998 | Hill et al. | |
| 5,827,358 A | 10/1998 | Kulish et al. | |
| 5,858,062 A | 1/1999 | McCulloh et al. | |
| 5,893,275 A | 4/1999 | Henry | |
| 5,893,944 A | 4/1999 | Dong | |
| 5,928,189 A | 7/1999 | Phillips et al. | |
| 5,979,440 A | 11/1999 | Honkonen et al. | |
| 6,010,555 A | 1/2000 | Smolarek et al. | |
| 6,162,283 A | 12/2000 | Conrad et al. | |
| 6,212,904 B1 | 4/2001 | Arkharov et al. | |
| 6,217,635 B1 | 4/2001 | Conrad et al. | |
| 6,287,366 B1 | 9/2001 | Derive et al. | |
| 6,302,107 B1 | 10/2001 | Richey, II et al. | |
| 6,311,719 B1 | 11/2001 | Hill et al. | |
| 6,314,957 B1 | 11/2001 | Boissin et al. | |
| 6,344,069 B2 | 2/2002 | Smolarek et al. | |
| 6,346,139 B1 | 2/2002 | Czabala | |
| 6,446,630 B1 | 9/2002 | Todd, Jr. | |
| 6,457,485 B2 | 10/2002 | Hill et al. | |
| 6,471,744 B1 * | 10/2002 | Hill | 95/19 |
| 6,478,857 B2 | 11/2002 | Czabala | |
| 6,511,526 B2 | 1/2003 | Jagger et al. | |
| 6,520,176 B1 | 2/2003 | Dubois et al. | |
| 6,544,318 B2 * | 4/2003 | Dee et al. | 95/96 |
| 6,551,384 B1 | 4/2003 | Ackley et al. | |
| 6,629,525 B2 | 10/2003 | Hill et al. | |
| 6,641,644 B2 | 11/2003 | Jagger et al. | |
| 6,651,653 B1 | 11/2003 | Honkonen et al. | |
| 6,651,658 B1 * | 11/2003 | Hill et al. | 128/204.23 |
| 6,681,764 B1 | 1/2004 | Honkonen et al. | |
| 6,691,702 B2 | 2/2004 | Appel et al. | |
| 6,698,423 B1 | 3/2004 | Honkonen et al. | |
| 6,712,087 B2 | 3/2004 | Hill et al. | |
| 6,712,886 B2 * | 3/2004 | Kim | 96/111 |
| 6,764,534 B2 | 7/2004 | McCombs et al. | |
| 6,802,889 B2 | 10/2004 | Graham et al. | |
| 6,805,729 B2 | 10/2004 | Lim et al. | |
| 6,811,590 B2 | 11/2004 | Lee et al. | |
| 6,866,041 B2 | 3/2005 | Hardy, Jr. et al. | |
| 7,066,985 B2 | 6/2006 | Deane et al. | |
| 7,135,059 B2 * | 11/2006 | Deane et al. | 96/115 |
| 2002/0053286 A1 | 5/2002 | Czabala | |
| 2002/0127442 A1 | 9/2002 | Connor et al. | |
| 2004/0020366 A1 | 2/2004 | Walker et al. | |
| 2004/0149133 A1 | 8/2004 | McCombs et al. | |
| 2005/0072426 A1 | 4/2005 | Deane et al. | |
| 2005/0081713 A1 * | 4/2005 | Lee et al. | 95/96 |

FOREIGN PATENT DOCUMENTS

| | | |
|---|---|---|
| WO | WO 98/58219 | 12/1998 |
| WO | WO 03/092817 | 11/2003 |

OTHER PUBLICATIONS

"AirSep lowers boom.", www.hmenews.com/2004.12/depts/vendors/vendors1.htm.

* cited by examiner

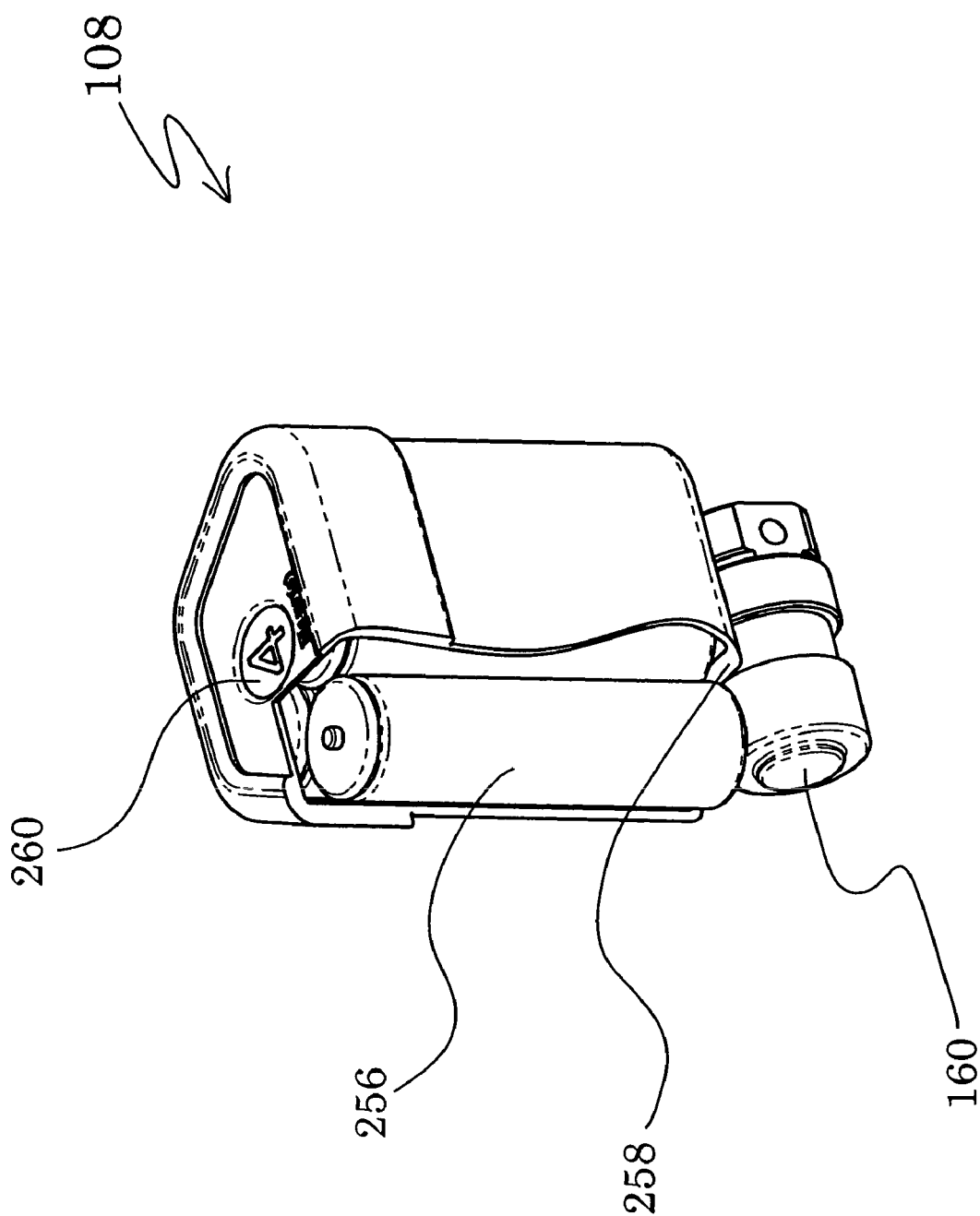

Section D-D

Section C-C

METHOD OF CONTROLLING THE RATE OF OXYGEN PRODUCED BY AN OXYGEN CONCENTRATOR

CROSS-REFERENCE TO RELATED APPLICATION(S)

Reference is hereby made to the following co-pending applications, which were filed on even date with the present application: "Ambulatory Oxygen Concentrator Containing a Power Pack", Theodore W. Jagger et al., application Ser. No. 11/054,622; "Adsorbent Cartridge for Oxygen Concentrator", Theodore W. Jagger et al., application Ser. No. 11/054,615; "Ambulatory Oxygen Concentrator Containing a Three Phase Vacuum Separation Process", Theodore W. Jagger et al., application Ser. No. 11/054,340; "Personal Oxygen Concentrator", Theodore W. Jagger et al., application Ser. No. 11/054,713; "Method of Providing Ambulatory Oxygen", Theodore W. Jagger et al., application Ser. No. 11/054,341; "Low Power Ambulatory Oxygen Concentrator", Theodore W. Jagger et al., application Ser. No. 11/054,716; "Ambulatory Oxygen Concentrator With High Efficiency Adsorbent", Theodore W. Jagger et al., application Ser. No. 11/054,367; "Portable Oxygen Concentrator With a Docking Station", Theodore W. Jagger et al., application Ser. No. 11/054,714; "Product Pump for an Oxygen Concentrator", Theodore W. Jagger et al., application Ser. No. 11/054,512; and "Method and Apparatus for Controlling the Purity of Oxygen Produced by an Oxygen Concentrator", Theodore W. Jagger et al., application Ser. No. 11/054,368.

BACKGROUND OF THE INVENTION

The field of this invention relates to oxygen concentrators. In particular, the invention relates to wearable oxygen concentration systems utilizing vacuum swing adsorption for creating an oxygen stream for ambulatory respiratory patients.

There is a need for home and ambulatory oxygen systems for use by patients. Supplemental oxygen is required for patients exhibiting symptoms from certain diseases and lung disorders; for example, pulmonary fibrosis, sarcoidosis, or occupational lung disease. For such patients, oxygen therapy is an increasingly beneficial prescription to help the patients live normal and productive lives. While not a cure for lung disease, prescriptive supplemental oxygen increases blood oxygenation, which reverses hypoxemia. Oxygen prescriptions prevent long-term effects of oxygen deficiency on organ systems, the heart, brain and kidneys. Oxygen treatment is also prescribed for Chronic Obstructive Pulmonary Disease (COPD), heart disease, AIDS, asthma, and emphysema.

Currently, supplemental medical oxygen for therapy is provided to a patient from high pressure gas cylinders; cryogenic liquid in vacuum-insulated containers or thermos bottles commonly called "dewars", and oxygen concentrators. Some patients require in-home oxygen only, while others require in-home as well as ambulatory oxygen depending on the prescription. The three systems are all used for in-home use. However, oxygen concentrators provide a special beneficial advantage because they do not require refilling of dewars or exchange of empty cylinders with full ones. Home oxygen concentrators, however, do have drawbacks. They consume relatively large amounts of electricity; are relatively large and heavy; emit excessive heat and are relatively noisy.

There has been a need for an improved portable device for supplying oxygen to a patient. Only small high pressure gas bottles and small liquid dewars are truly portable enough to be used for ambulatory needs. Either system may be used for both in-home and ambulatory use. A patient using a stationary oxygen system at home (or even a portable system which cannot be readily transported), who travels must opt for small cylinders towed in a wheeled stroller or for portable containers that they carry, typically on a shoulder sling. Both of these options have significant drawbacks.

A major drawback of the cylinder option is that small cylinders only provide oxygen for a short duration. Moreover, these cylinders are maintained at a high pressure, and thus their use is restricted due to safety considerations. Another drawback of the cylinders is the refill requirement after depletion of the contents of the cylinder. Empty cylinders must be refilled at specialized facilities, or in the patient's home using a commercial oxygen concentrator which extracts oxygen from the air. The latter option requires an on-site compressor to boost the output pressure of the concentrator to meet cylinder refill pressure requirements. Filling of cylinders with oxygen in the home is potentially dangerous due to the physics involved with compressing gas. Another detriment to cylinder usage is fire hazards associated with storage of large volumes of oxygen in the home environment.

Convenience and safety issues are not the only drawbacks associated with the use of cylinders. Another drawback is the cost associated with cylinders. Cylinders require special care, and specialized materials are required for high pressure oxygen compatibility, which in turn drives up the cost of cylinder-based systems.

The liquid oxygen storage system also has drawbacks. The primary drawback is the requirement of a base reservoir which necessitates refilling once a week or more from an outside source. Liquid oxygen is transferred from the base unit to a portable dewar, which is used by an ambulatory patient. However, there is substantial waste, as a certain amount of oxygen is lost during the transfer to the portable containers and from evaporation. Up to twenty percent of the contents of the base cylinder is lost in the course of two weeks because of losses in transfers and normal evaporation. Even without withdrawal by the patient, the base reservoir will typically boil dry over a period of one to two months.

The aforementioned systems all require are filling station. When the patient is out in public, such stations are not readily available. Upon running low (or out) of oxygen, the patient must return home to a specified place that can refill the system. Such a requirement detracts from the ambulatory usefulness of the systems.

The industry has developed a set of recommendations for systems targeted to provide portable oxygen for ambulatory patients. The Fifth Oxygen Consensus Conference set forth the following standards for long-term oxygen therapy ambulatory equipment: 1) equipment must weigh less than 10 lbs., 2) equipment must provide the equivalent of 2 liter/min of continuous flow $O_2$, and 3) the flow rate must be maintained for four hours or more. Thus, ambulatory equipment, or personal oxygen systems (POS), are to be inconspicuous to the public as well as unrestricting to the patient. Cylinders and other liquid oxygen systems tend to be bulky, which interferes with normal daily activities. Similarly, cylinders and liquid oxygen systems are difficult to conceal from public view. Ideally, a POS is small, lightweight, quiet, and flexible which allows the device to be concealed from the public. The present invention, whereby oxygen rich gas is provided to a patient from a wearable oxygen concentrator, meets and exceeds these standards.

BRIEF SUMMARY OF THE INVENTION

A method of providing concentrated oxygen product gas to a patient comprises producing product gas by a vacuum swing adsorption (VSA) process through a plurality of separation columns connected to a vacuum source driven by a motor. Separated product gas is then pumped to a reservoir in which the pressure is monitored and used to adjust the speed of the motor based on that pressure. The separated gas is then delivered to the patient.

BRIEF DESCRIPTION OF THE DRAWINGS

FIG. 11 is a perspective view of the components contained within a battery module.

DETAILED DESCRIPTION

The current invention relates to separation of gases using vacuum swing adsorption. Specifically, disclosed is an oxygen concentrator for a patient who requires a source of oxygen. The present invention is further explained with reference to the drawn figures in which like structures are referred to by like numerals throughout the several views.

Overview—Oxygen Concentrator 100 (FIGS. 1-4)

Figure 1:
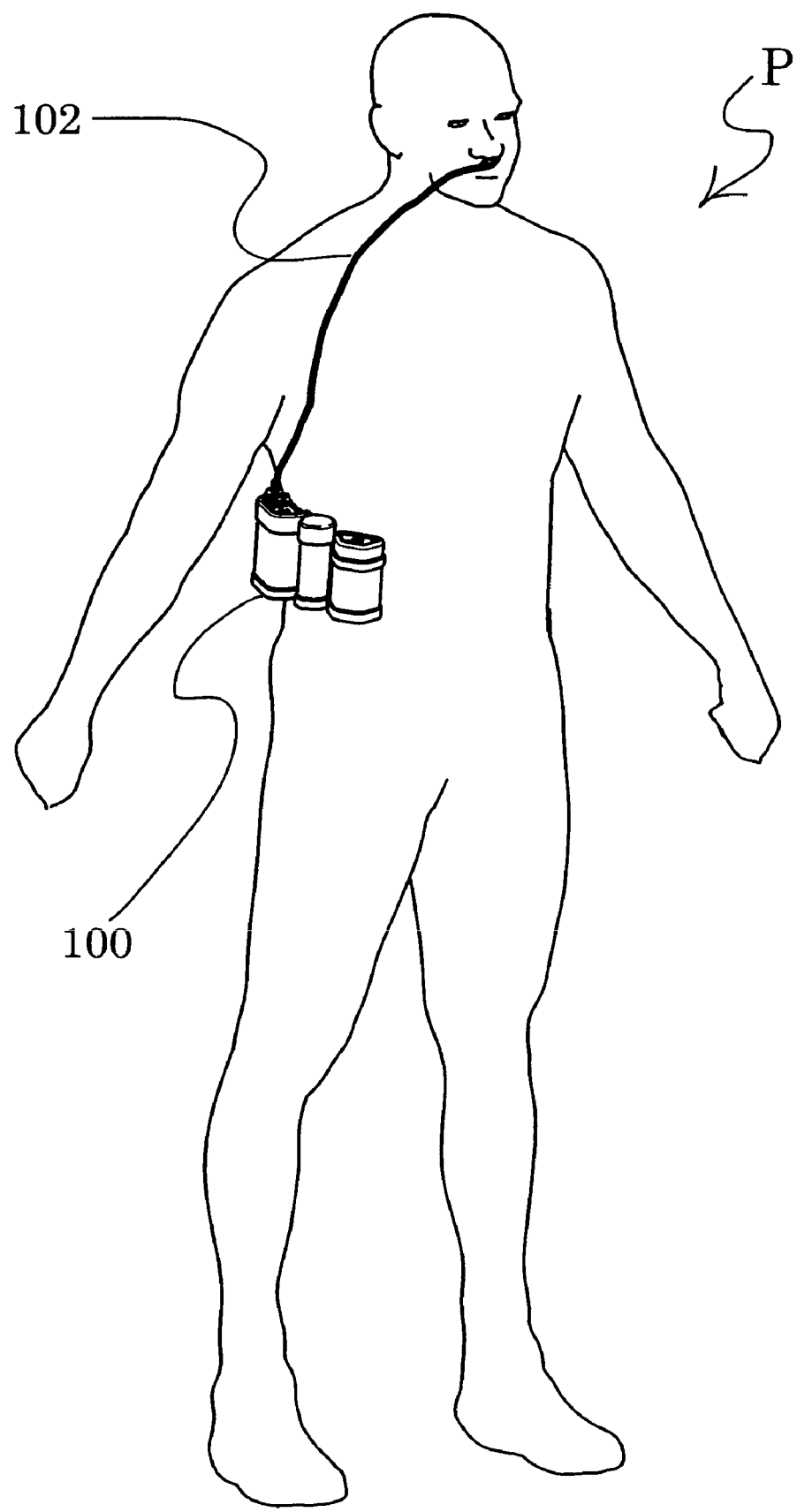
FIG. 1 is a front view of a patient carrying the oxygen concentrator of the present invention.

FIG. 1 is a front view showing patient P with oxygen concentrator 100 and oxygen delivery tube 102. Oxygen concentrator 100 is a small unit which utilizes vacuum swing adsorption to separate oxygen from the ambient air around patient P. Oxygen concentrator 100 is compact and light so as not to interfere with the ambulatory movement of patient P, and can produce a product stream of gas containing a range of eighty-five to ninety-five percent oxygen.

Oxygen delivery tube 102 is a polymer tube or similar oxidation resistant structure, which extends from oxygen concentrator 100 to the nose, mouth, or port into the upper airway of patient P. Tube 102 allows delivery of oxygen to patient P for inhalation. In FIG. 1, patient P is about six foot tall to illustrate an approximation of the relative size of oxygen concentrator 100.

Figure 2:
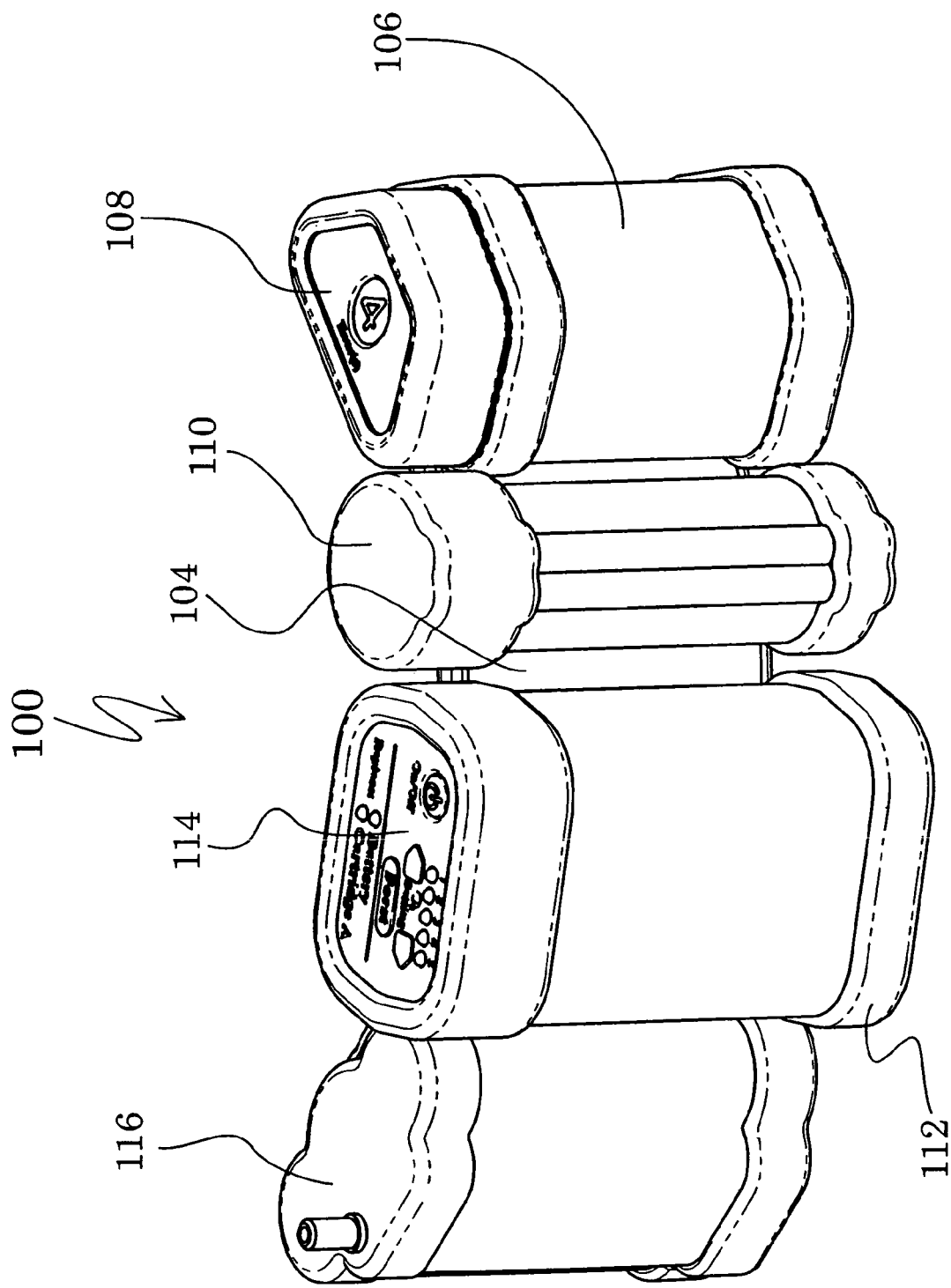
FIG. 2 is a front perspective view of the oxygen concentrator.

FIG. 2 is a perspective view of oxygen concentrator 100. Oxygen concentrator 100 is comprised of belt 104, power module 106 containing power pack 108, reservoir module 110, control module 112 containing user interface 114, and separation cartridge module 116. Oxygen concentrator 100 is a portable oxygen separator used to provide an oxygen rich gas stream to patient P. Belt 104 connects and carries the modules 106, 110, 112, and 116 of oxygen concentrator 100. Belt 104 may contain belt loops (not illustrated), clips, or a pair of straps that contain a buckle and holes or like fastening device for securing oxygen concentrator 100 to patient P. Alternatively, oxygen concentrator 100 may be placed in a purse, fannypack, or similar personal carrying device for transport with patient P.

Power module 106 provides the necessary power to operate the systems of oxygen concentrator 100. In the embodiment illustrated, power module 106 contains replaceable power pack 108. Reservoir module 110 stores oxygen rich gas that has been separated from ambient air by cartridge module 116. Control module 112 pilots and regulates the interaction of the power module 106, reservoir module 110, and separation cartridge module 116 of oxygen concentrator 100. User interface 114 on control module 112 is a console which allows patient P to adjust and monitor oxygen concentrator 100.

Figure 3:
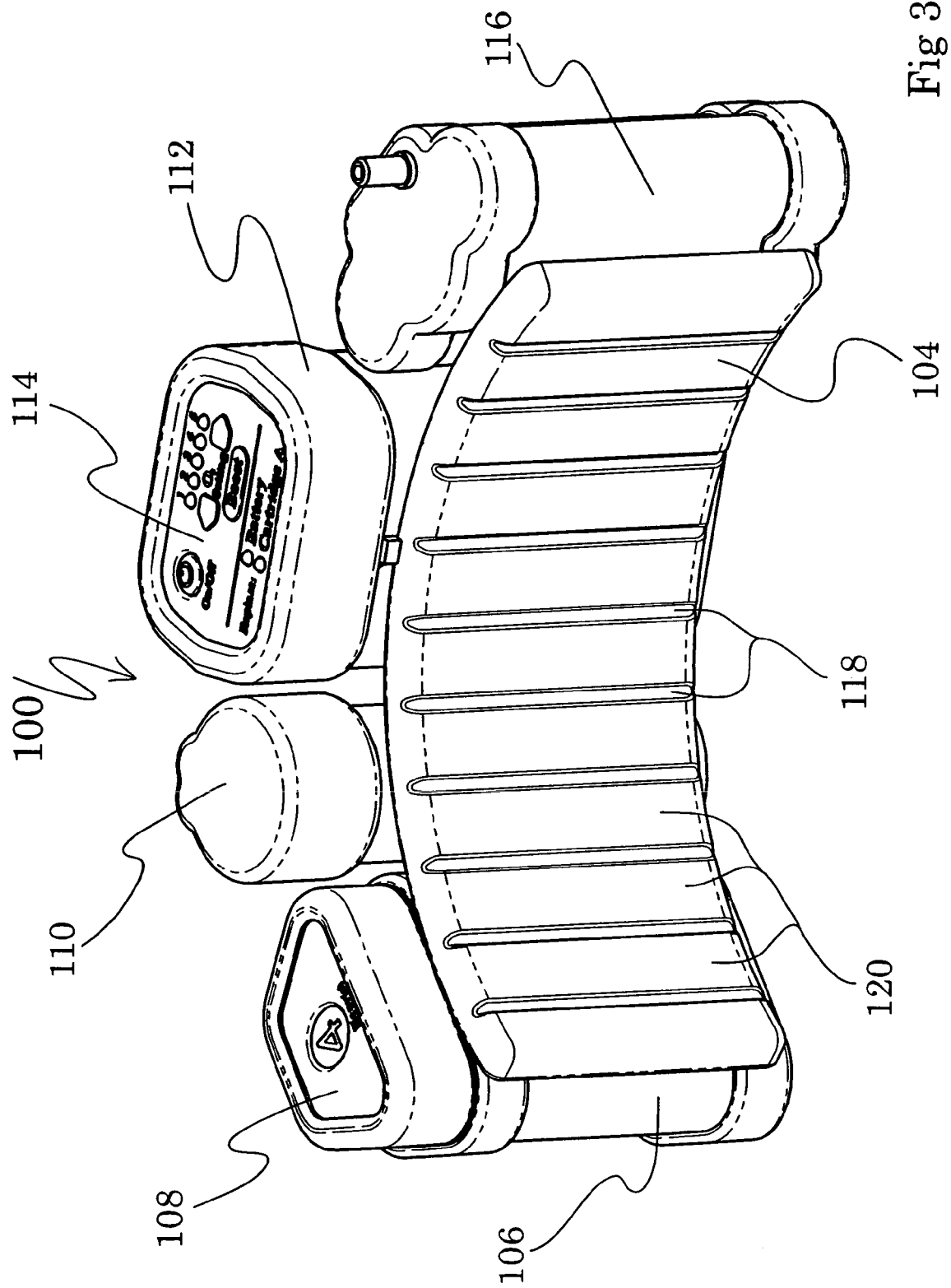
FIG. 3 is a rear perspective view of the oxygen concentrator.

FIG. 3 is a perspective view of the opposite side of oxygen concentrator 100 as shown in FIG. 2. Illustrated in FIG. 3 are belt 104, power module 106, reservoir module 110, control module 112, and separation cartridge module 116. Belt 104 is constructed to contain belt segments 120 formed by serrations 118. This allows the belt 104 to be flexible and conform to patient P's body while wearing oxygen concentrator 100. Belt 104 is fabricated from a flexible material, such as textile or plastic and contains an inner padding such as foam. Belt 104 also houses the electrical and pneumatic connections of oxygen concentrator 100.

Figure 4:
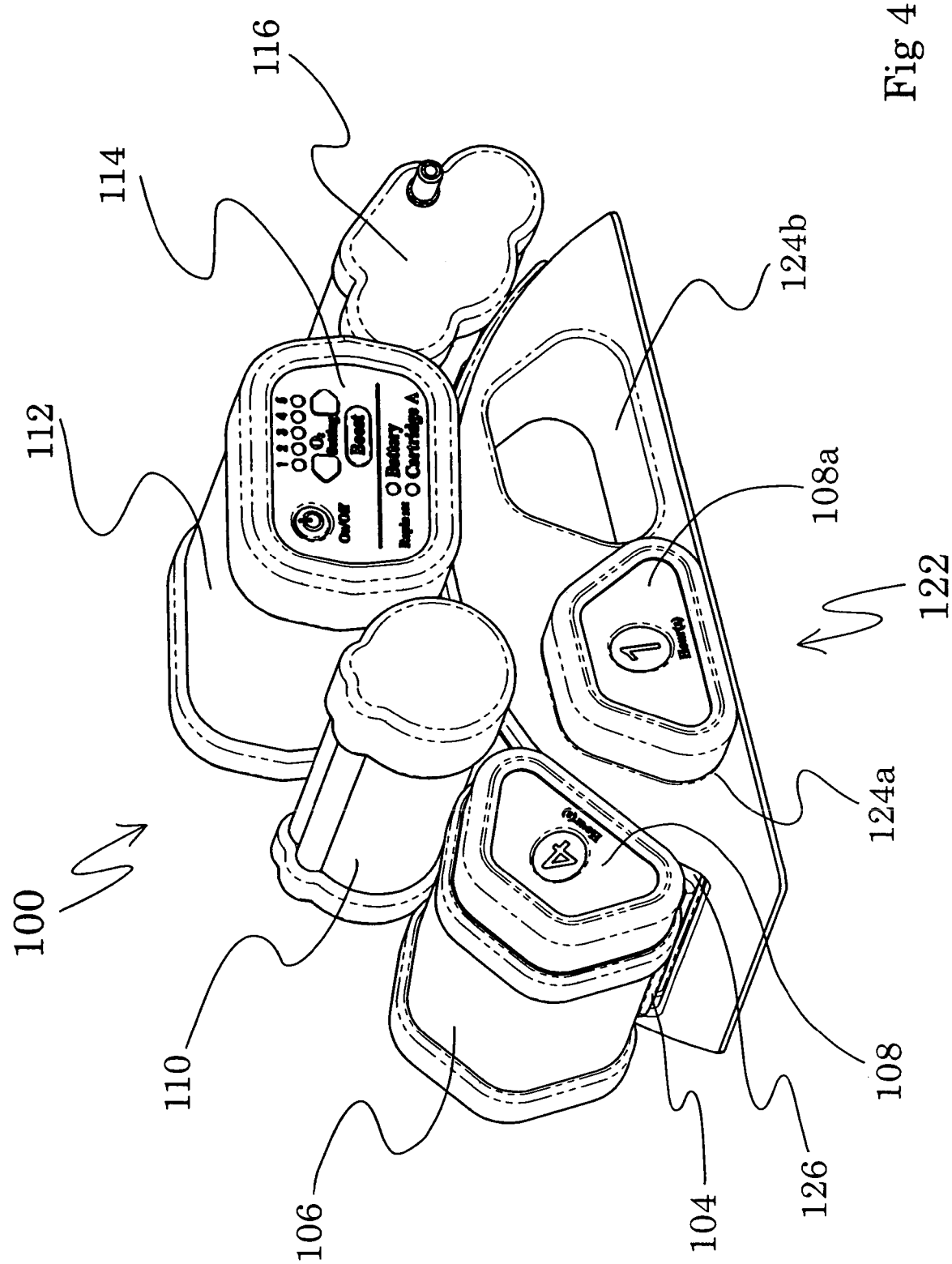
FIG. 4 is a front perspective view of the oxygen concentrator and a docking station.

FIG. 4 is a perspective view of the front side of the oxygen concentrator 100 on docking station 122. Illustrated are oxygen concentrator 100 comprising belt 104, power module 106, reservoir module 110, control module 112, and separation cartridge module 116, along with docking station 122 containing power pack chargers 124a and 124b. Belt 104 is flexible and thus rests on the arc shaped docking station 122. Docking station 122 contains power pack chargers 124a (with power pack 108a inserted therein) and 124b, as well as concentrator dock 126 which supports the oxygen concentrator 100 while on the docking station 122. Docking station 122 converts AC power to recharge power packs 108.

Figure 5:
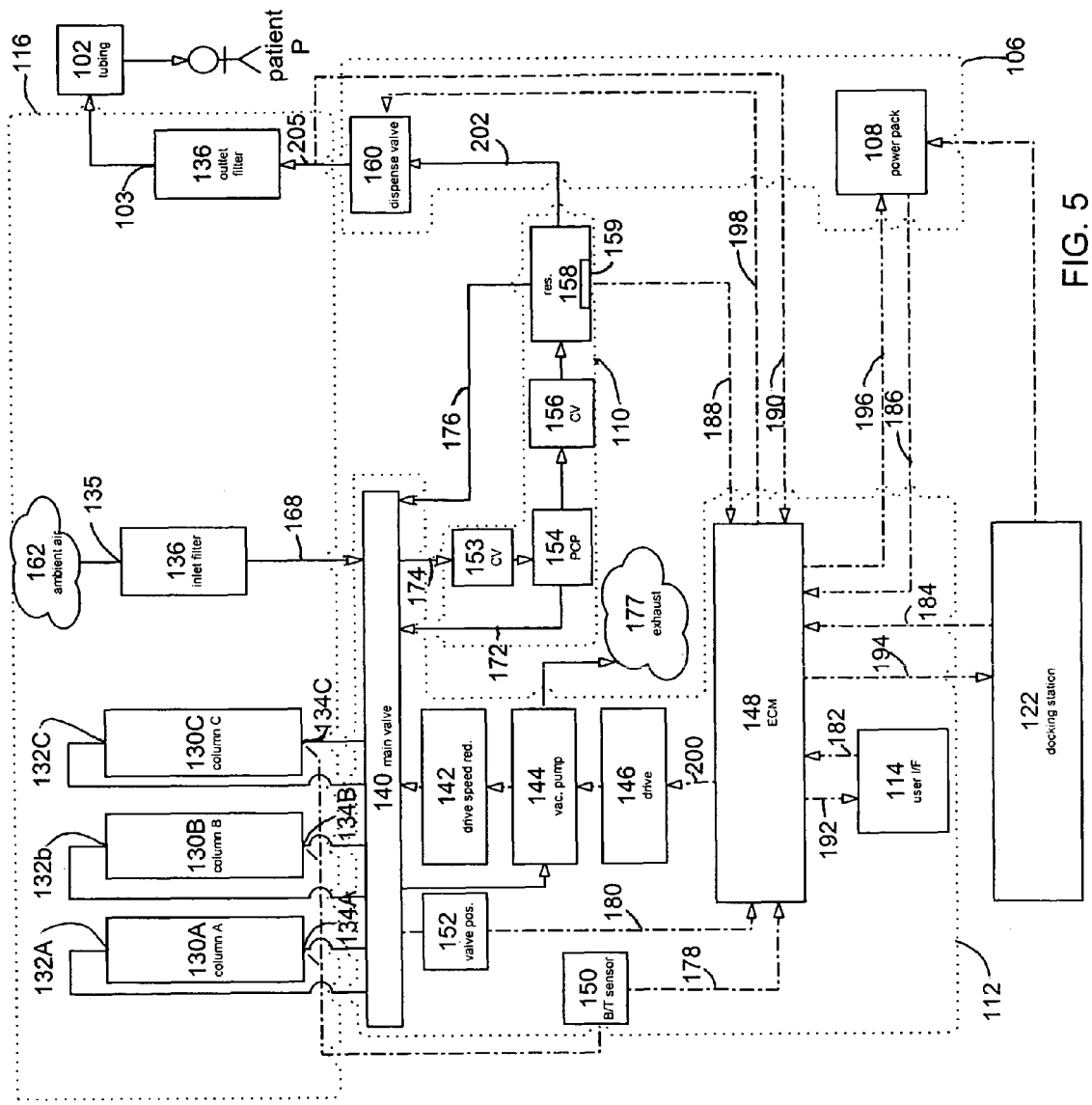
FIG. 5 is a block diagram showing the components and connections of the oxygen concentrator.

Oxygen Concentrator 100 System Components and Connections (FIG. 5)

FIG. 5 is a block diagram of oxygen concentrator 100 illustrating power module 106, reservoir module 110, control module 112, and separation cartridge module 116, along with docking station 122 and showing the components and connections among the modules and docking station 122. Oxygen concentrator 100 components includes product gas outlet port 103, adsorbent columns 130a-130c (each containing a respective inlet port 132a-132c and a respective outlet port 134a-134c), air inlet port 135, air inlet filter 136, product gas final filter 138, main valve 140, drive reducer 142, vacuum pump 144, drive 146, electric control module (ECM) 148, breakthrough flow sensor 150, valve position sensor 152, product control pump 154, check valve 156, main storage reservoir 158 containing pressure sensor 159, dispensing valve 160, as well as previously identified components tubing 102, power pack 108, user interface 114, and docking station 122.

As shown in FIG. 5, adsorbent cartridge module 116 includes adsorbent columns 130a-130c each containing respective inlet ports 132a-132c and outlet ports 134a-134c, air inlet filter 136, and product gas final filter 138. Ambient air enters air inlet port 135, passes through air inlet filter 136, and enters valve 140 for distribution to adsorbent columns 130a-130c. Product gas passes through final filter 138 and product gas outlet port 103 into tubing 102 for delivery to patient P. Inlet ports 132a-132c of adsorbent columns 130a-130c connect to valve 140 through inlet lines 164a-164c. Similarly, outlet ports 134a-134c connect to valve 140 through outlet lines 166a-166c.

Control module 112 houses main valve 140, drive reducer 142, vacuum pump 144, drive 146, electric control module (ECM) 148, breakthrough flow sensor 150, valve position sensor 152, and contains user interface 114. Main valve 140 is pneumatically connected to adsorbent columns 130a-130c, as well as inlet filter 136 via inlet line 168, vacuum pump 144 via vacuum inlet line 170, product control pump 154 via vacuum line 172 and product gas line 174, and main reservoir 158 via product gas line 176. Valve 140 is actuated by drive 146 through a motor speed reducer 142. Also, valve 140 connects to breakthrough flow sensor 150 and valve position sensor 152 which send electrical inputs 178 and 180 to ECM 148.

ECM 148 is a logic control, such as a PLC (programmable logic controller), microprocessor, or similar structure which controls operation of oxygen concentrator 100. ECM 148 contains the set of inputs and outputs associated with the modules for regulating oxygen concentrator 100. ECM 148 also receives control setting inputs 182 and 184 from user interface 114, and docking station 122, respectively, power pack management input 186 from power pack 108, reservoir pressure input 188 from pressure sensor 159 in main reservoir 158, and nasal pressure input 190 from dispensing valve 160. ECM 148 provides interface output 192 to the user interface 114, interface output 194 to docking station 122, power management output 196 to power pack 108, dispensing valve time open output 198 to dispensing valve 160, and motor drive output 200 to drive 146.

User interface 114 contains physical controls such as dials, toggle switches, push button switches, and similar controls, for operating oxygen concentrator 100. The physical controls provide electrical control settings to ECM 148. ECM 148 reads these settings as inputs 182 and provides output 192 to the user interface 114. The status is converted from electric signals to physical output by indicator lights, status display, and similar structures of user interface 114.

Power pack management input 186 and output 196 control the charge and discharge of voltage from power pack 108 to drive 146 via ECM 148. Drive 146 will activate vacuum pump 144, valve 140 through drive speed reducer 142, and any other systems requiring power. Power pack management output 196 will also supply power to indicator lights, status display, audible alarm (if included), and other passive electrical system requirements on user interface 114 through ECM 148.

ECM 148 controls and coordinates the steps of the vacuum swing adsorption cycle through its inputs and outputs. In one embodiment, breakthrough flow sensor 150 provides an input 178 into ECM 148 by measuring air flow rates. The position of valve 140 is detected by valve position sensor 152 to produce input 180. Reservoir 158 contains a sensor to produce reservoir pressure input 188. Dispensing valve 160 also contains a pressure sensor which provides nasal pressure input 190 in response to differential pressure. ECM 148 reads these inputs to control the cycle by changing outputs, such as motor drive output 200 for drive 146. Drive 146 propels vacuum pump 144. Vacuum pump 144 creates a vacuum that is communicated to valve 140 through vacuum input line 170, while dispelling nitrogen rich gas as exhaust 177. Another output 198 controls the time that dispensing valve 160 is open. In this embodiment, the inputs and outputs are connected to a PLC within ECM 148 which is programmed to control the cycle of oxygen concentrator 100.

Contained within reservoir module 110 is an oxygen-rich gas accumulator comprising reservoir 158, check valve 156, product control pump 154, and check valve 153. Reservoir 158 receives oxygen-rich gas produced by oxygen concentrator 100 and stores it at a low pressure above ambient until it is required for use. A portion of the stored oxygen-rich gas is delivered back to valve 140 by product gas line 176 for use in ordering the nitrogen content in adsorbent columns 130a-130c by moving much of the residual nitrogen held after evacuation near the outlets 134a-134c toward inlets 132a-132c of the columns 130a-130c. Reservoir 158 is in communication with dispensing valve 160 through product gas line 202. Check valve 156 opens to allow oxygen into reservoir 158 and closes to prevent backflow of oxygen upon reaching the desired pressure in reservoir 158.

Product control pump 154 is driven by vacuum provided by the vacuum pump 144 through valve 140 via vacuum line 172. Product line 174 is in communication from separation cartridge module 116 to check valve 153, which opens to allow product control pump 154 to transport separated oxygen-rich gas to reservoir 158. Product control pump 154 delivers the product gas to main reservoir 158 through check valve 156.

Dispensing valve 160 and power pack 108 are contained within power module 106. Dispensing valve 160 is used to feed the flow of oxygen-rich gas to the patient P by delivery of the product gas through final product gas line 205 to product final filter 138. The product gas is obtained from the main reservoir 158 through product gas line 202. Power pack 108 provides the power supply for oxygen concentrator 100 as previously described. Power pack 108 is rechargeable through docking station 122 as represented by power connection 204.

Vacuum Swing Adsorption (VSA) Process—Overview

Oxygen concentrator 100 operates using a vacuum swing adsorption process, which involves a series of cycles that include a feed step or phase, an evacuation step or phase, and a repressurization step or phase. Each of these three phases takes place in one of the three columns 130a-130c at any given time. Each column 130a-130c is in a different phase. For purposes of explanation, the VSA process will be described in reference to "column 130", which is representative of each of the three columns 130a-130c.

In the feed phase, a gas stream of ambient air 162 enters inlet end 132 of column 130 while product gas containing concentrated oxygen is delivered from outlet end 134 of column 130. The slight vacuum in column 130 draws air 162 into column 130 and through an adsorbent material (typically a zeolite) which preferentially retains specific components of air (nitrogen), allowing the desired product (oxygen) to pass through. A mass transfer zone (MTZ), which is a small region in which nitrogen is being adsorbed, is passing through the adsorbent material. The MTZ divides the column 130 into two segments: a nitrogen-rich segment where the MTZ has passed through, and an oxygen-rich segment ahead of the moving MTZ. The MTZ forms at the inlet 132 at the start of the process and gradually moves through the column to the outlet 134 as the process proceeds. Outlet end 134 of column 130 is connected to main reservoir 158 through main valve 140, check valve 153, and product control pump 154, so that oxygen-rich product gas from column 130 is pumped into reservoir 158.

In the evacuation phase, column 130 is brought to a stronger vacuum by vacuum pump 144, causing the adsorbed component, i.e. nitrogen, to be desorbed. The nitrogen is evacuated from column 130 through main valve 140, and is discharged by vacuum pump 144 as waste exhaust 177.

In the repressurization phase, the previously evacuated column 130 is returned to near 1 atm. Ambient air 162 enters column 130 through inlet end 132, and recycled product gas from product line 176 enters column 130 through outlet end 134. The gases replace the vacuum that was previously drawn in column 130 during the evacuation phase. Just prior to column 130 reaching about 1 atm, the repressurization phase ends and the feed phase of the cycle begins again.

This constitutes the general principles of vacuum swing adsorption (VSA) for gas separation. All phases can be accomplished with a single column, or with a plurality of columns. If a plurality of columns are used, it is preferable to have a multiple of three (illustrated as 130a-130c in FIG. 5) that are sequenced out of phase for the different cycle phases in order to maintain constant product flow.

The Feed Phase—Breakthrough Detection

During the feed phase of the separation cycle, the position of the MTZ within adsorbent column 130 is monitored, determined, and beneficially used to control the termination of the feed phase. The control results in improvements in product purity and recovery with concomitant decrease in energy consumed, as well as system size and system weight for a given volume of product produced.

Breakthrough is defined as the point when the MTZ reaches outlet 134 of adsorbent column 130. At this point, feed gas begins to flow into the separated product gas stream. This is undesirable because the purity of the product stream is reduced by the feed stream gas if the feed is allowed to continue past this point. Conversely, if the feed phase is terminated before the MTZ nears outlet 134 of column 130, product recovery will be reduced because product gas contained in column 130 between the MTZ and outlet 134 of column 130 will be subjected to the evacuation phase that follows the feed phase in the separation cycle, and much of this remaining product gas will be lost with the desorbed gas in the waste stream.

For a particular column geometry, temperature, adsorbent type and condition, and cycle vacuum levels, there is an optimal time during the feed phase of the cycle to terminate the feed—before purity requirements are compromised, but after the maximum possible product has been recovered from column 130. This optimal time is determined by the detection of the passage of the mass transfer zone through a specific position relative to outlet end 134 of column 130.

For some combinations of system variables, the optimum feed termination time corresponds to the beginning of breakthrough when the leading edge of the MTZ has just reached outlet end 134 of column 130. This event can be detected by monitoring either or both of the gas flow rates at inlet 132 or outlet 134 to column 130. Before breakthrough, the outlet flow rate is less than the inlet flow rate by an amount equal to the rate of nitrogen gas adsorption of column 130 from the feed gas flow. After breakthrough, column 130 is no longer adsorbing nitrogen from the feed gas, so the inflow and outflow rates of column 130 become equal. Any method of measuring gas flow rates to determine the point in time when these flow rates begin the transition toward equality can be used to detect this beginning of breakthrough.

It has been determined that if the inflow rate of air to column 130 is maintained constant, a simple detection of a significant rise in slope of the outflow rate marks breakthrough. Conversely, if the outflow rate is held fairly steady, then a falling slope of the inflow rate marks the breakthrough. Monitoring the ratio of flow for the inlet and outlet and detecting a significant change in the ratio of flows toward a ratio of 1:1 can mark breakthrough in systems where inflow or outflow may not be steady enough to detect breakthrough by monitoring just one of the flow rates.

For other combinations of system variables, the optimum feed termination time may correspond to the MTZ position prior to breakthrough. In these cases, it is beneficial for a specific amount of product to be intentionally left in column 130 at the end of a feed phase. Detecting the position of the MTZ before breakthrough can be accomplished by additional methods.

One method used determines the volume of gas passed into or out of adsorbent column 130 up to the point of breakthrough by integrating the flow rate during the time interval between an initial feed and breakthrough while using some breakthrough detection method as previously described. Volume of flow may also be directly measured by physical equivalent methods using displacements of known volumes. Once the volume of gas that passes the column up to the point of breakthrough is determined, the volume of gas flow can be monitored during subsequent feed phases and the feed terminated when the volume reaches a specific value less than that for breakthrough. At anytime during the feed phase, the volume of gas passed through column 130 since the beginning of feed divided by the volume of gas at breakthrough will be the same ratio as the position of the mass transfer zone divided by the length of column 130 (assuming a constant cross sectional area along the length). Using this relationship, the position of the MTZ within column 130 can be adequately determined during the feed phase.

The components of oxygen concentrator 100 as previously described are used to complete the cyclical phases of VSA to separate gases. The feed phase operates at a slight vacuum just below ambient (in the range of 0.9 to 1 atm). This provides just enough driving force to pull ambient air 162 into adsorbent column 130 through inlet filter 136. The vacuum is caused by product control pump 154, which is driven by the vacuum drawn by vacuum pump 144. Product control pump 154 is a piston pump or similar structure that meters a volume of gas. Product control pump 154 connects with a volume much greater than the piston displacement volume, such as main reservoir 158.

The feed phase is allowed to proceed until breakthrough is detected. Up to this point, the outflow gas from adsorbent column 130 has been a high purity oxygen/argon, low percent nitrogen mixture. The MTZ position is controlled to minimize nitrogen into the product gas mixture. The MTZ position is monitored by breakthrough flow sensor 150, which detects a large increase in flow rate associated with breakthrough when the nitrogen no longer is preferentially adsorbed by adsorbent column 130. Breakthrough flow sensor is located near the column inlet 132, column outlet 134, or similar place where the flow rate being measured is accessible. When the increase MTZ flow is detected, a signal is sent to ECM 148, which also receives valve position signal 180 from the valve position sensor 152. The ECM 148 compares the timing of the MTZ breakthrough signal and the valve position signal and makes a minor adjustment to motor speed 200 based on lead, lag, or on-time status to keep the breakthrough time near the end of each feed phase. Alternately, ECM 148 receives a signal from breakthrough flow sensor 150 and immediately terminates the current feed phase in column 130 by signaling valve 140 to rotate to start the next phase. In yet another embodiment, the separation system contains a shut off valve that is signaled to close the feed of ambient air 162 into column 130, or the delivery of product gas from the column upon breakthrough detection.

In another embodiment, the method for determining the position of the mass transfer zone prior to breakthrough is accomplished by placing a small amount of non-adsorbing material within adsorbent column 130 at a particular position. When the mass transfer zone passes through this position, a flow change is detectable as the adsorption of gas is briefly interrupted by the non-adsorbing segment of column 130. The resulting flow change is detectable using the same methods for breakthrough detection previously described.

With larger columns and slower feed phases, the position of the mass transfer zone has been established by measuring temperature rise at positions of interest within column 130. Significant temperature increases result from the heat of adsorption at the MTZ and can be detected by thermistors or similar devices placed within column 130.

The Evacuation Phase

The evacuation phase brings the gas in adsorbent column 130 that was just in the feed phase to a vacuum state. At the end of the feed phase, the adsorbent column 130 is in equilibrium with the air infeed mixture near 1 atm from column inlet 132 up to the MTZ. Hence, if the ending position of the MTZ is established, and the nitrogen, oxygen, and argon isotherms for the chosen adsorbent mass are known, then the quantity of these gases present in adsorbent column 130 at the end of each feed phase is known. Vacuum pump 144 draws a vacuum on adsorbent column 130. This vacuum level is determined and set to a state that will remove a large portion of the gas left in column 130. In one embodiment, this is 0.2 to 0.3 atm. By percentage, the vast majority of gas discharged is nitrogen. The evacuated gas is discharged as waste from exhaust 177 of vacuum pump 144. The preferred embodiment uses a fixed displacement type of vacuum pump 144. During each evacuation phase, the adsorbed gas in column 130 is expanded into a much larger volume made up of the column volume plus the fixed displacement volume of pump 144.

The evacuate phase creates a self regulating effect that compensates for reductions in the amount of nitrogen adsorbed by adsorbent column 130 as the adsorbent degrades (ages). If the adsorbent loses efficiency, less nitrogen will be present in column 130 at the end of the phase, but the volume of the pump that the nitrogen expands into remains the same. A stronger vacuum will result that will remove more nitrogen and therefore allow more air to be fed during the next feed phase. A more constant breakthrough time results and provides a more robust product cycle.

The evacuation is provided by vacuum pump 144, which is controlled and activated by drive 146. The volume removed for each cycle of the vacuum pump 144 will remain constant, but the motor drive output 200 will be controlled by the rate of product gas used by patient P. The amount of oxygen used by patient P depends on the patient P's on-demand respiratory rate, which is sensed by the device and from a variable position switch which sends an input 192 from user interface 114 to ECM 148, which in turn provides motor drive output 200 to drive 146. This determines the speed of each successive phase and, therefore, the oxygen production rate.

In one embodiment, a purge is applied at the very end of an evacuation phase. While still in the evacuation phase, a purge of product gas (mostly oxygen) introduced through outlet 134 effectively drives out a portion of nitrogen in column 130 through inlet 132. Adding the purge gas of high purity oxygen/argon through outlet 134 desorbs more nitrogen from outlet 134 of column 130, and pushes the nitrogen toward inlet 132 of adsorbent column 130 and creates an ordering of the gases. The purge volume is a function of vacuum level and adsorbent characteristics. A purge portion of the evacuation phase is not a necessary phase for a functioning device, but allows high oxygen purity to be maintained with weaker vacuum levels.

The Repressurization Phase

The repressurization phase brings adsorbent column 130 (just previously evacuated and purged) tip to the feed pressure. In one embodiment, the gas used for repressurization is from both the infeed ambient air 162 and a counter stream from the (oxygen-rich) product gas line 176 from the main reservoir 158. Alternately, the repressurization of product gas can be accomplished through valve design negating the need for a separate line. The product gas is dispensed from a stream of product gas from the adsorbent column that is in the feed phase through a vacuum break valve used during repressurization. Repressurization with product gas can be done before, simultaneously, or after partial pressurization with ambient air. Repressurization with product gas is done at the opposite end of column 130 as repressurization with ambient air 162.

The effect of adding the repressurization gas of high purity oxygen/argon through outlet 134 creates a cleaning zone at outlet 134 of adsorbent column 130 where, during the feed phase that follows next, any stray nitrogen can be preferentially adsorbed and not discharged as product gas. This improves the ordering of gases in the adsorbent column 130. By repeating this phase during successive cycles, the purity will continue to increase in the product output. Weaker vacuums require more oxygen volume returned to column 130 during repressurization if high purity is desired. That is, a stronger vacuum must be drawn on the column 130 to effectuate the same purity of oxygen absent the use of oxygen-rich gas as aback flush for repressurization at the outlet 134 of column 130. At the end of repressurization, the feed phase will proceed.

Figure 6:
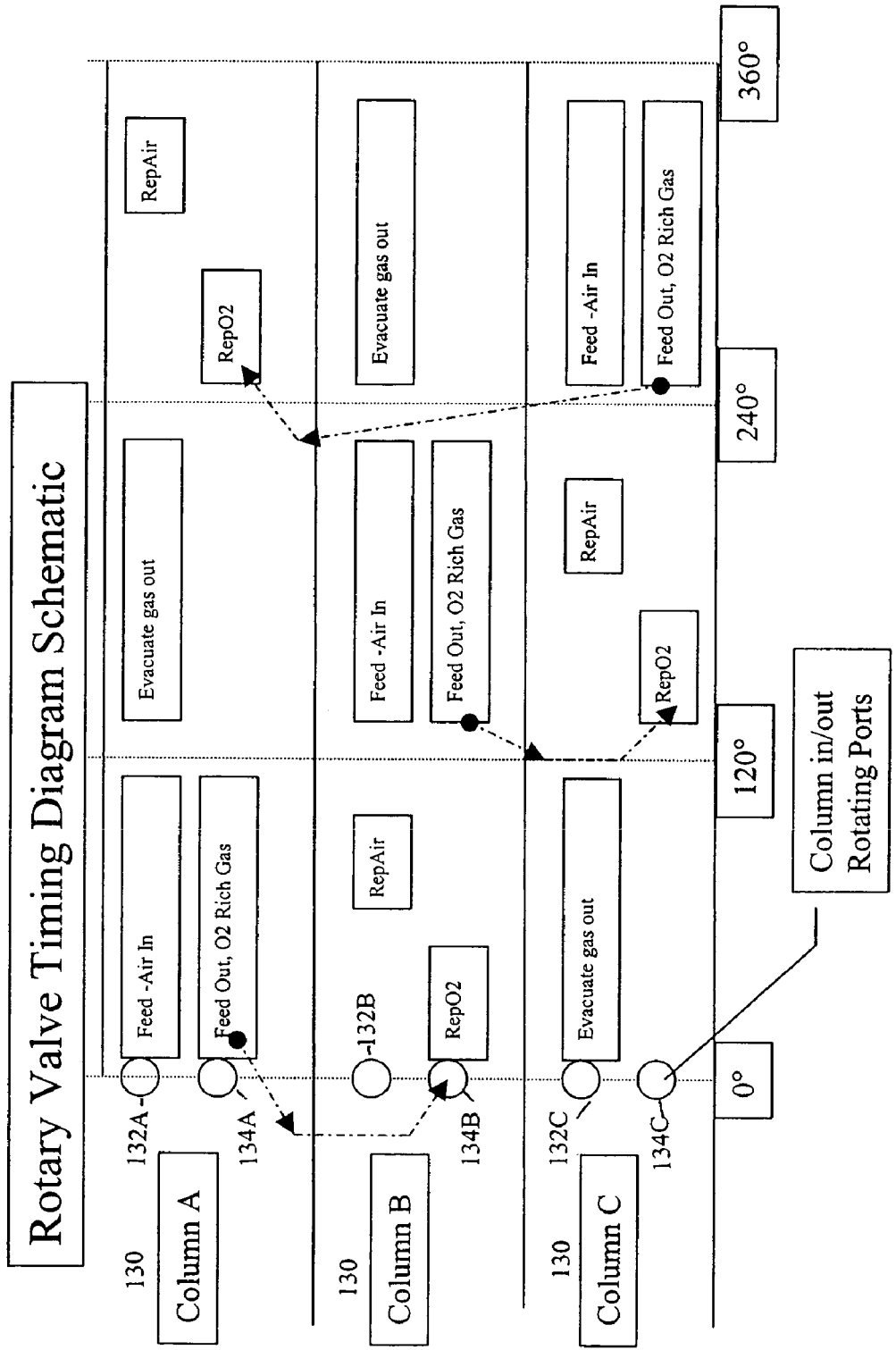
FIG. 6 is a diagram showing rotary valve timing.

Valve 140 Timing (FIG. 6)

The VSA cycle comprises three phases: evacuation, repressurization, and feed, which occur sequentially in each column 130a-130c. For clarity, only column 130a will be discussed, although each phase is performed (at different times during a complete cycle) in each of columns 130a-130c.

Starting with the evacuation phase of the cycle, a small amount of oxygen (not illustrated) may flow into outlet 134a of adsorption column 130a to purge adsorption column 130a, while vacuum pump 144 withdraws gas present at inlet 134a of the column, i.e. nitrogen-rich gas.

During the repressurization phase, an amount of previously separated oxygen flows into outlet 134a of adsorption column 130a for a short time, and then air is allowed to enter inlet 132a of column 130a that has been previously evacuated. There may be a slight overlap of the oxygen flow into outlet 134a of adsorption column 130a and the air flow in the opposite direction into inlet 132a. Air freely flows into inlet 132a of adsorption column 130a upon opening of valve 140 as adsorption column 130a has been previously evacuated during the evacuation phase.

During the feed phase, air continues to flow into inlet 132a of adsorption column 130a while oxygen is removed from outlet 134a of column 130a by a pressure differential created by product control pump 154. As the MTZ passes through the adsorption column and reaches a position at or near outlet 134a, vacuum pump 144 will again begin to evacuate adsorbent column 130a and restart with the evacuation phase. In the embodiment illustrated in FIG. 6, these phases are controlled by main valve 140.

FIG. 6 is a diagram showing timing for main valve 140, which is a rotary valve that moves 360° (one full revolution about a central axis) for each complete cycle of the VSA process. In the embodiment with three columns 130a-130c, the timing for each phase of the cycle is 120°. Each column 130a-130c is present in a different phase for each 120° of rotation of valve 140 that is different from the other two columns to obtain a sequence that creates a steady flow of oxygen as valve 140 keeps rotating.

As shown in the timing diagram, adsorption column 130a is in the feed phase of the cycle at a start point of zero degrees. Air is being let in through inlet filter 136 and column inlet 132a while separated gas consisting of highly concentrated oxygen is being removed through column outlet 134a. A portion of the oxygen-rich product gas is used in the repressurization of column 130b. Adsorption column 130b is in the repressurization phase at a point of rotary valve 140 being in initial position zero degrees. As valve 140 is turned, column outlet 134b is fed with the oxygen-rich gas for a portion of the valve's rotation, preferably less than 120°. After the flow of oxygen-rich gas enters column 130b through the column outlet 134b, air repressurization through the opening of column inlet 132b begins. In the embodiment shown, this takes place at a point after valve 140 has begun its rotation and ends before it reaches a third of its rotation, or a 120° rotation.

While column 130a is in feed phase and column 130b is in the repressurization phase, column 130c is in the evacuation phase. During the evacuation phase, a vacuum is drawn to remove adsorbed gas through inlet 132c, thereby regenerating it for the following feed phase.

In the embodiment shown, each column 130a, 130b, and 130c, is in a different phase of the cycle as one moves vertically down the diagram in FIG. 6. During the first one hundred twenty degrees of rotation of the rotary valve, column 130a is in the feed phase. Simultaneously, from zero to one hundred twenty degrees of rotation, column 130b is being repressurized, while column 130c is being evacuated.

For the next one hundred twenty degrees of rotation of valve 140 (i.e., from 120° to 240°), adsorption column 130a is in the evacuation phase. At this same time, column 130b is in the feed phase, and column 130c is in the repressurization phase.

Moving horizontally across the diagram for column 130a, during the final one hundred twenty degrees of rotation of valve 140 (i.e., from 240° to 360°), column 130a is repressurized first using separated gas, and then ambient air. Separated gas and ambient air are introduced to the column 130a through column inlet 132a and column outlet 174a at opposite ends of column 130a. During the final one hundred twenty degrees of rotation (i.e. from 240° to 360°) of main valve 140, column 130b is in the evacuation phase, and column 130c is in the feed phase. Upon reaching three hundred sixty degrees, valve 140 is back at its starting position (zero degrees), and the cycles for each column 130a-130c restart from the zero degree position.

Oxygen Concentrator 100 Physical Components (FIGS. 7-16)

Figure 7:
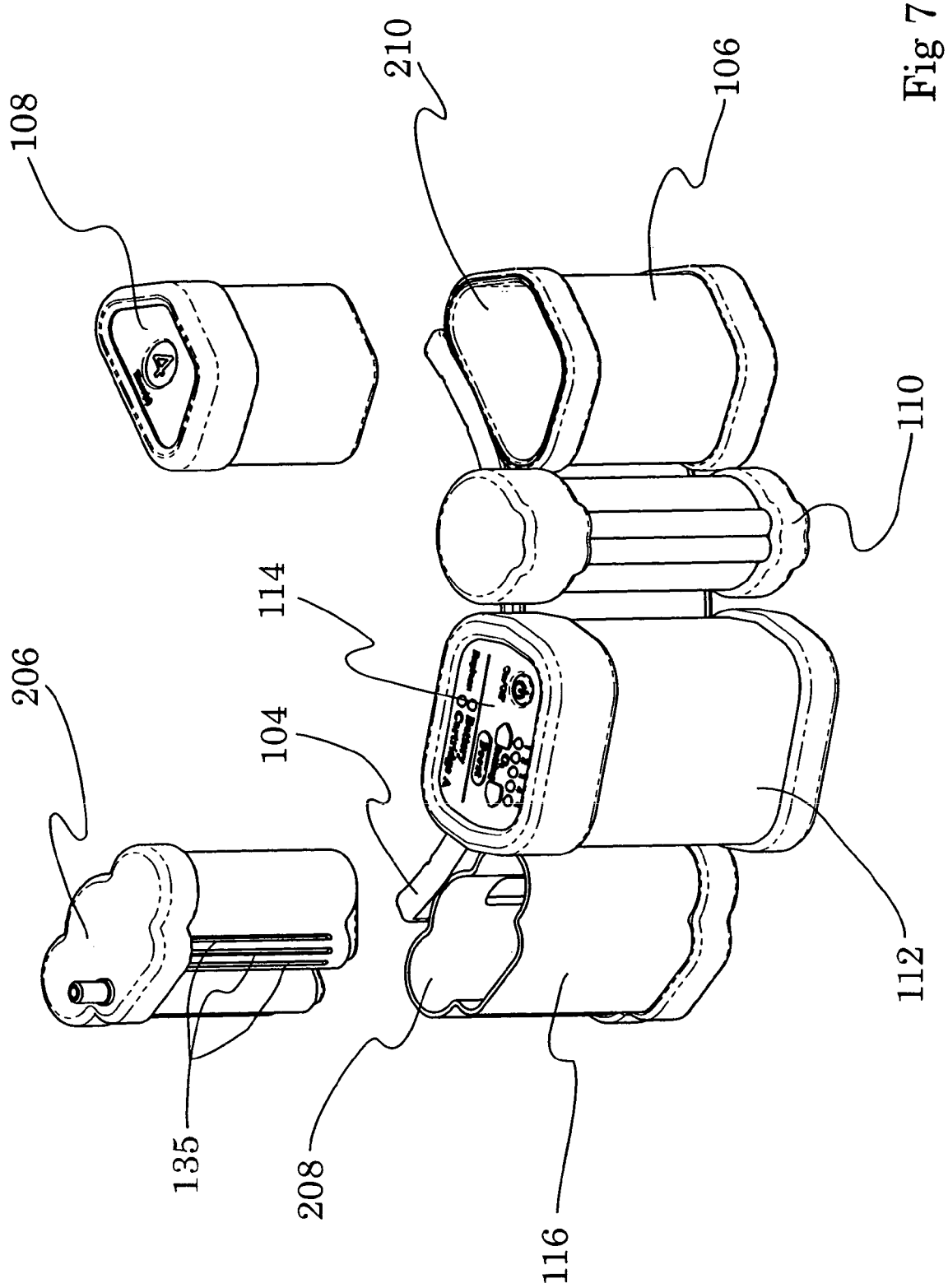
FIG. 7 is an exploded view of the oxygen concentrator in which the power pack and the adsorbent cartridge have been removed.

FIG. 7 shows an exploded view of the oxygen concentrator 100, which includes belt 104, power module 106 containing removable power pack 108, reservoir module 110, control module 112, and separation cartridge module 116 containing adsorbent cartridge 206. Power pack 108 has been removed from receptacle 210 of power module 106. Adsorbent cartridge 206 has been removed from receptacle 208 of cartridge module 116. Adsorbent cartridge 206 and power pack 108 are easily removable to facilitate replacement.

In this embodiment, power pack 108 is a rechargeable battery. Receptacle 210 contains electrical contacts (not illustrated) for connection to power pack 108. Cartridge 206 contains a quick-connect attachment (not illustrated) for inlet lines 164a-164c, outlet lines 166a-166c, inlet air line 168, and final product gas line 205 (not illustrated) within receptacle 208. Also present on cartridge 206 are air inlet ports 135 which receive ambient air 162 for separation. Adsorbent cartridge 206 contains adsorbent material that deteriorates in efficiency as it is used and ages.

Figure 8:
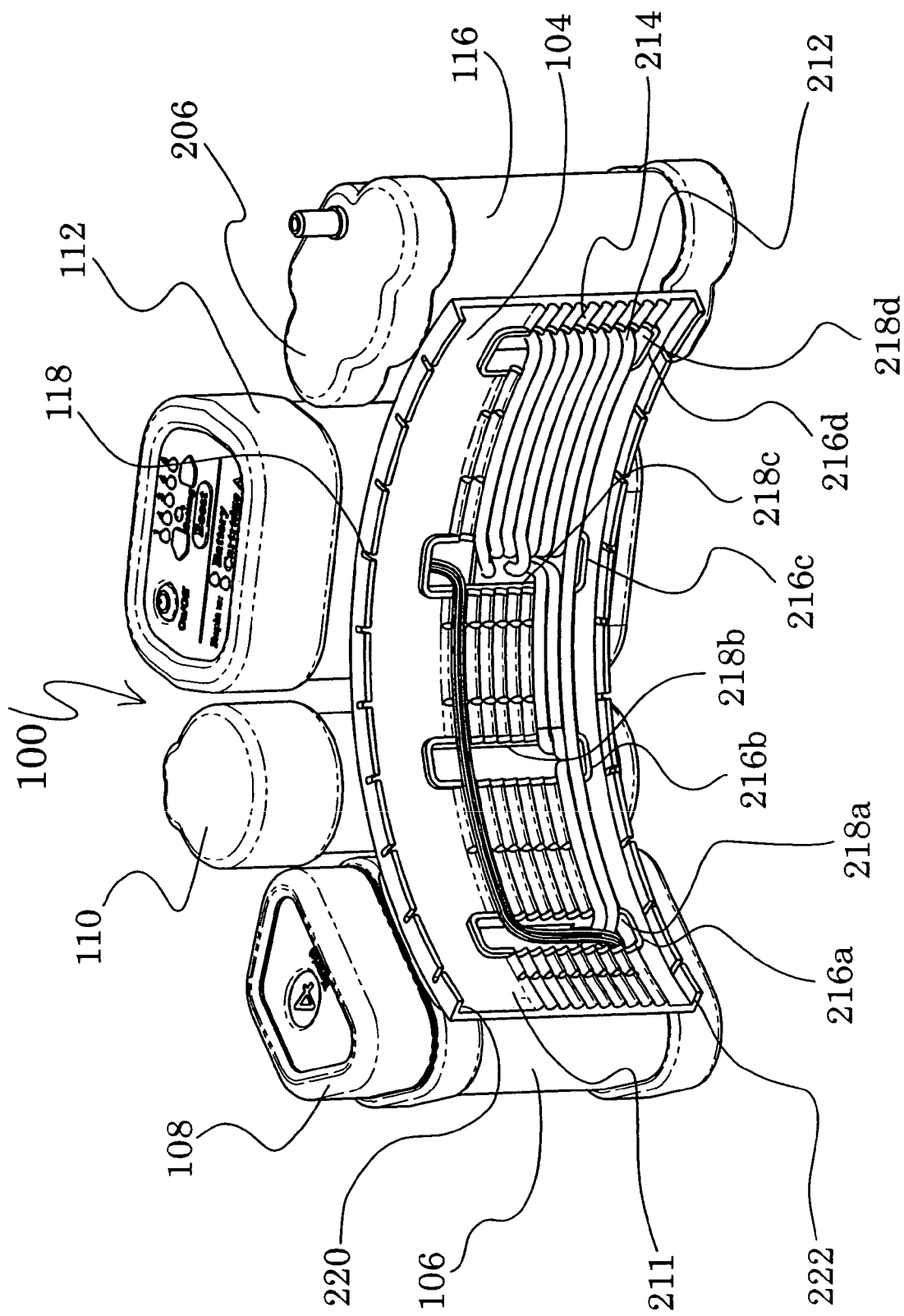
FIG. 8 is a perspective view of the oxygen concentrator with a portion of the belt removed.

FIG. 8 is a perspective view of oxygen concentrator 100. A portion of belt 104 has been removed revealing back interior surface 211 and inner connections amongst the modules, including utility tubes 212, tube pathways 214, module apertures 216a-216d, and module sockets 218a-218d.

Utility tubes 212 run between the adjacent modules and contain either electrical wiring or pneumatic lines, or comprise pneumatic lines and electrical wiring and associated connections. Tubes 212 are constructed to be flexible and bend as belt 104 is manipulated. If the tubes 212 contain electrical lines, the tubes are constructed from a dielectric material to insulate electrical wires, or similar material commonly used in electrical connections. If the tubes 212 comprise pneumatic lines, they may be air tight, small diameter polyvinyl or PVC tubes to connect the various gas input, gas separation, and gas removal systems of the oxygen concentrator 100. Tubes 212 contain openings or connections as required for electrical and pneumatic communication with each module. The back interior surface 211 of belt 104 contains tube pathways 214. Pathways 214 fabricated on the interior surface 211 of belt 104 allow the utility tubes 212 to extend between the modules 106, 110, 112, and 116. Tube pathways 214 create a semi-partitioned area on back interior surface 211 of belt 104 which support tubes 212.

Belt 104 is fabricated to contain apertures 216a-216d which allow modules 106, 110, 112, and 116 to connect utility tubes 212 of belt 104 through sockets 218a-218d. Apertures 216a-216d and sockets 218a-218d are fabricated as part of modules 106, 110, 112, and 116. Serrations 118 can be seen between the upper and lower edges 220 and 222 of belt 104. When fabrication of belt 104 is completed, padding will be inserted between edges 220 and 222, and material will be wrapped around creating serrations 118 and belt segments 120 to complete belt 104 as illustrated in FIG. 3. The padding is fabricated over the top of tubes 212 and tube pathways 214, or separately fabricated and fastened to back interior surface 211 during assembly of belt 104. Individual modules allow the device to flex when mounted about a curved surface, such as a belt around patient P's waist. The construction of belt 104 with tubes 212 allows patient P to manipulate the oxygen concentrator 100, such as by bending belt 104 to wear around the waist, place on docking station 122, or folding concentrator 100 in half for transport in a carryall.

Figure 9:
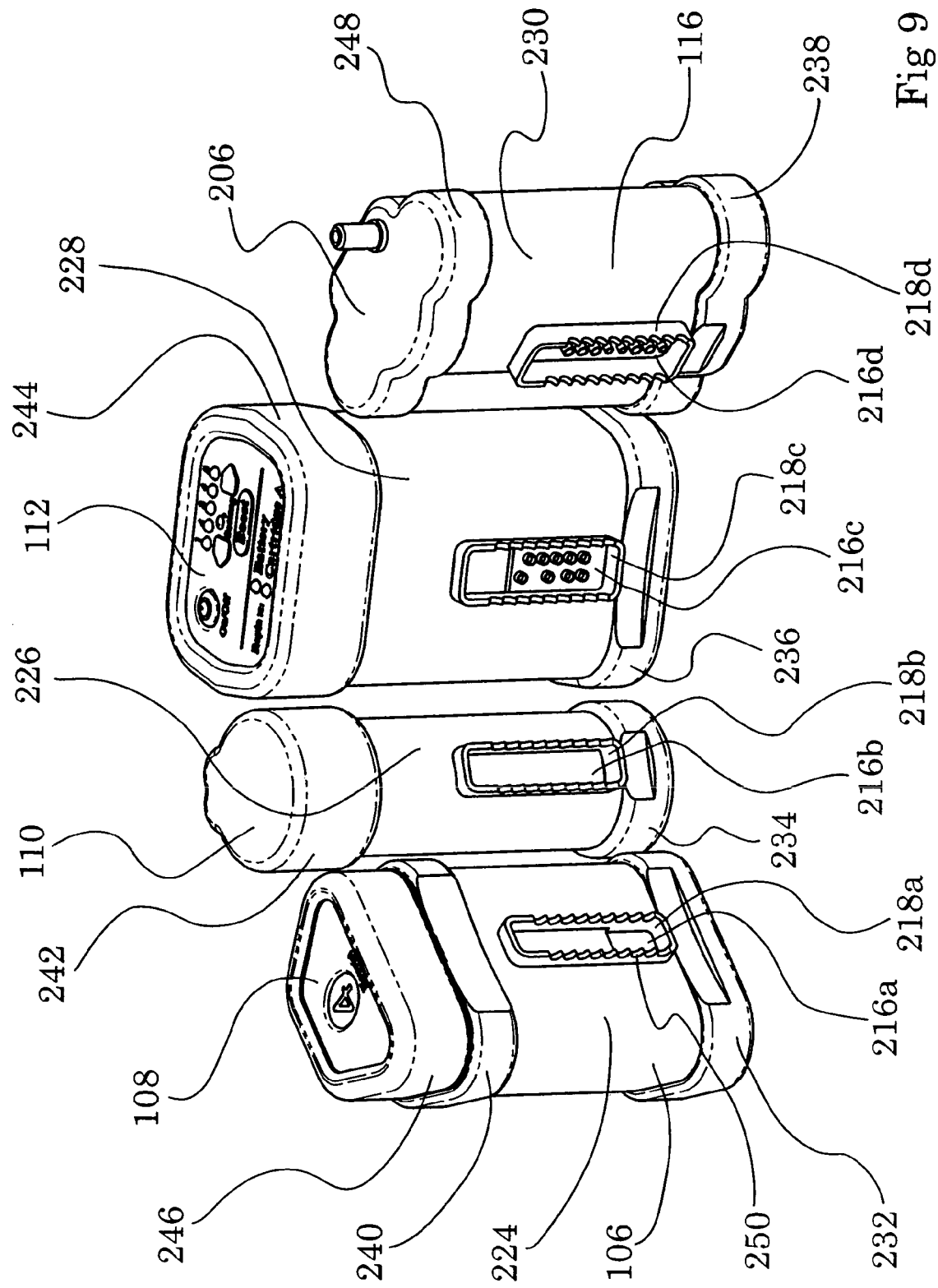
FIG. 9 is a perspective view of the components of the oxygen concentrator without the belt.

FIG. 9 is a perspective view of modules 106, 110, 112, and 116 of oxygen concentrator 100. In this view, belt 104 has been removed to illustrate the positions of sockets 218a-218d containing apertures 216a-216d on each respective module 106, 110, 112, and 116. Each respective module 106, 110, 112, and 116 is constructed from a thermoplastic material such as acrylanitrile butadine styrene (ABS) or high density polyethylene (HDPE), or a lightweight metal or a similar rigid material that is oxidation resistant.

Each module 106, 110, 112, and 116, comprises a case portion 224, 226, 228, and 230, defining the outer volume of each respectively. Bottom padding 232, 234, 236, and 238, covers the lower base portion of each module 106, 110, 112, and 116, respectively. Similarly, top padding 240 extends around the top perimeter of power module 106, while top padding 242 and 244 covers the top portions of modules 110 and 112. Power pack top padding 246 covers the top portion of power pack 108 and cartridge top padding 248 covers the top of separation cartridge 206. Padding 222-248 is a foam or similar lightweight material that adds protection to the modules as well as acts to reduce vibration of oxygen concentrator 100 felt by patient P. Alternately, oxygen concentrator 100 is enclosed in soft, flexible material to further increase comfort and maintain flexibility. In one embodiment, padding 232-248 is fabricated separately from the modules 106, 110, 112, and 116, power pack 108 and cartridge 206. In assembling the oxygen concentrator 100, padding 232-248 and case portions 224, 226, 228, and 230, are merged and secured either using fasteners, adhesives, or a manufacturing process such as ultrasonic welding.

Case portions 224, 226, 228, and 230, of each of the modules 106, 110, 112, and 116, contain sockets 218a-218d fabricated on the surface that contacts belt 104. Socket 218a-218d for each module is constructed to have support paths 250 for electrical wiring and pneumatic tubing similar to those contained within belt 104 represented by tube pathways 214. Sockets 218a-218d are constructed so that support paths 250 on sockets 218a-218d align with tube pathways 214 in belt 104 when each individual module 106, 110, 112, and 116, is connected to belt 104. In one embodiment, sockets 218a-218d are constructed to allow each individual module 106, 110, 112, and 116, to snap onto belt 104 or attach in a similar quick connect fashion. Utility tubes 212 comprise quick connects at module apertures 216a-216d. Apertures 216a-216d are openings in the case portions 224, 226, 228, and 230, provided for connection of utility tubes 212 to components contained within each module 106, 110, 112, and 116. This allows for removal of a single module 106, 110, 112, or 116 should a specific component require maintenance or replacement. Sockets 218a-218d are constructed from the same material as the case portions 224, 226, 228, and 230.

Figure 10:
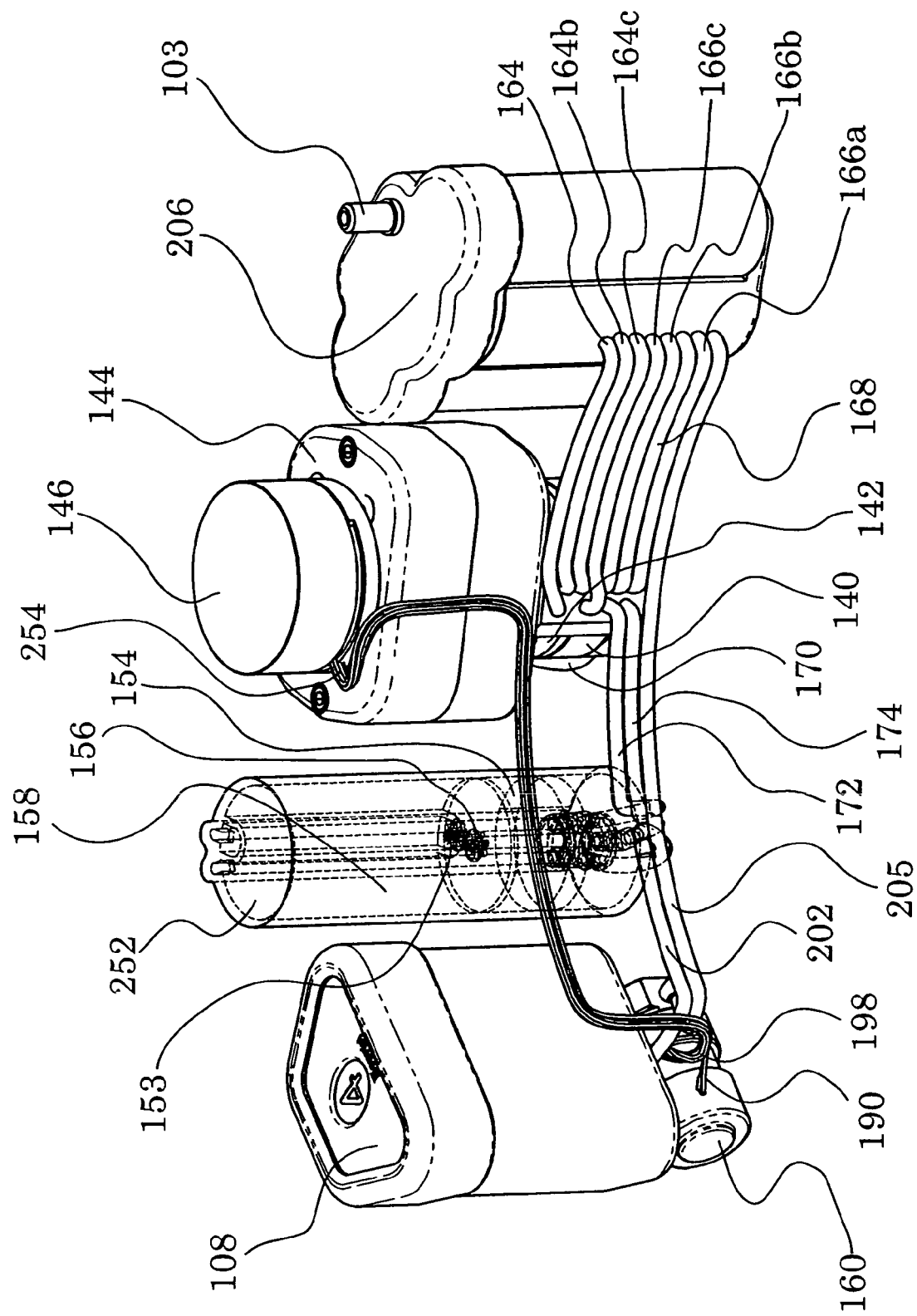
FIG. 10 is a perspective view of the components contained within the case portions of the modules and their associated pneumatic and electrical connections of the oxygen concentrator.

FIG. 10 is a perspective view of the components contained within modules 106, 110, 112, and 116, and the associated pneumatic and electrical connections of oxygen concentrator 100. Illustrated are power pack 108, valve 140, drive reducer 142, vacuum pump 144, drive 146, oxygen accumulator 252 (comprising product control pump 154, check valves 153 and 156, and reservoir 158), dispensing valve 160 connected to nasal pressure sensor line 190 and dispensing valve open line 198, column inlet lines 164a-164c, column outlet lines 166a-166c, product control pump vacuum line 172, product control pump inlet line 174, product gas line 202, final product gas line 205, adsorbent cartridge 206, and main electrical cable 254.

Main electrical cable 254 contains a set of electrical wires that carry inputs 178, 180, 182, 188, and 190, outputs 192 and 198, and power lines 186, 198, and 200 shown in FIG. 5. Main electrical cable 254 extends from power pack 108 to ECM 148 (not visible in FIG. 10). Dispensing valve time open output 198 and nasal pressure sensor input 190 are wires that extend between ECM 148 and dispensing valve 160. Similarly, the other inputs and outputs are wired to the appropriate system components as illustrated in FIG. 5 (although not specifically illustrated in FIG. 10.)

Product gas line 202 connects dispensing valve 160 with reservoir 158 of accumulator 252. Final product gas line 205 connects dispensing valve 160 to product gas outlet port 103 for connection to delivery tube 102 after passing through final filter 136 located in adsorbent cartridge 206 to provide patient P with oxygen rich product gas. Product control pump inlet line 174 extends from main valve 140 to product control pump 154, which pumps separated oxygen rich gas into reservoir 158. Vacuum line 172 connects product control pump 154 through valve 140 to a vacuum drawn by vacuum pump 144, and provides the actuation for product control pump 154. Column inlet lines 164a-164c and column outlet lines 166a-166c connect main valve 140 with column inlet ports 132a-132c and column outlet ports 134a-134c of columns 130a-130c, respectively (not illustrated). Inlet air line 168 transports ambient air 162 from separation cartridge 206 to main valve 140, while vacuum inlet line 170 connects vacuum pump 144 to main valve 140. All lines 164a-164c, 166a-166c, 168, 170, 172, 174, 176, 202, and 205, are pneumatic lines or similar structures that allow for the isolated flow of gases between system components.

FIG. 11 is a perspective view of the components contained within power module 106: power pack 108 (comprising cells 256, outer wall 258, and power pack life indicator 260) and dispensing valve 160. In the embodiment illustrated, power pack 108 is a lithium-ion battery pack comprised of five cells 256. Individual cells 256 are contained within outer wall 258, part of which has been removed to show cell 256. Power pack 108 is a battery that is rechargeable and removable from power module 106. Although illustrated as a trapezoid containing five cylindrical cells, the shape and number of cells will vary depending on the shape of power module 106 and power requirements of oxygen concentrator 100.

Power pack 108 is a lithium based battery pack capable of being recharged in a recharging socket or station that connects to an external power supply. Alternatively, power pack 108 comprises a battery or fuel cell. In one embodiment, power pack 108 is a lithium ion battery pack that is constructed from several interconnected lithium-ion batteries. Oxygen concentrator 100 uses a maximum of fifteen watts of power. This results in a battery weight of less than 0.7 pounds (0.3 kg). In this embodiment, patient P taking twenty breaths per minute at a setting of 2 liters per minute equivalent can use oxygen concentrator 100 for a minimum of four hours on a fully charged battery. Power pack 108 is easily exchanged with another similar battery pack, and can be removed with a simple pulling or tugging motion. In another embodiment (not illustrated), oxygen concentrator 100 contains a jack for receiving a power cord which can then be plugged into either a 110 volt wall outlet or a 12 volt power supply system (such as a car utility plug) so that power pack 108 can be charged in place in oxygen concentrator 100.

Power pack life indicator 260 displays the amount of time left that the power pack will operate the oxygen concentrator 100. As illustrated, power pack life indicator 260 is a display, such as a liquid-crystal display (LCD) or light emitting diode (LED) screen, with numeric output of expected life in hours. The LCD or LED screen may also contain a series of bars that act as indicators. Alternately, power pack life indicator 260 is a light or series of lights.

Dispensing valve 160 is contained within power module 106 and is used to feed the flow of oxygen to patient P. Dispensing valve 160 is a valve activated by a change in pressure, such as that caused when a person is inhaling. A sensor in the dispensing valve circuit monitors pressure, and opens dispensing valve 160 when a drop in pressure is sensed. ECM 148 communicates with dispensing valve 160 through input 190 and output 198 (see FIG. 5). Dispensing valve 160 is in communication with reservoir 158 through product gas line 202. Reservoir 158 is kept at a slight pressure above ambient. Thus, when dispensing valve 160 is opened, oxygen rich gas will flow from reservoir 158 through final product gas line 205, final product filter 138, and product gas outlet port 103 for delivery to patient P through tubing 102. The flow of gas is further assisted by the pressure drop created by patient P's inhaling. Dispensing valve 160 can be set to deliver oxygen rich gas to patient P for the beginning portion of a breath when patient P first inhales rather than the whole breath.

Dispensing valve 160 provides for operating oxygen concentrator 100 in one of two possible modes: pulse flow or continuous flow. When patient P is using the oxygen concentrator 100 in the pulse flow mode, dispensing valve 160 will open intermittently in response to inhalation and will stay open for a pulse time according to the setting of the controls as set by patient P. If continuous flow is desired, dispensing valve 160 is maintained at an open or partially opened state. The product is dispensed to patient P though oxygen delivery tube 102 at a continuous rate, typically in the range of 1-1.5 lpm (liters per minute). The pressure difference corresponding to a dispensing orifice in delivery tube 102 will accommodate the flow rate from the reservoir 158.

Figure 12D:
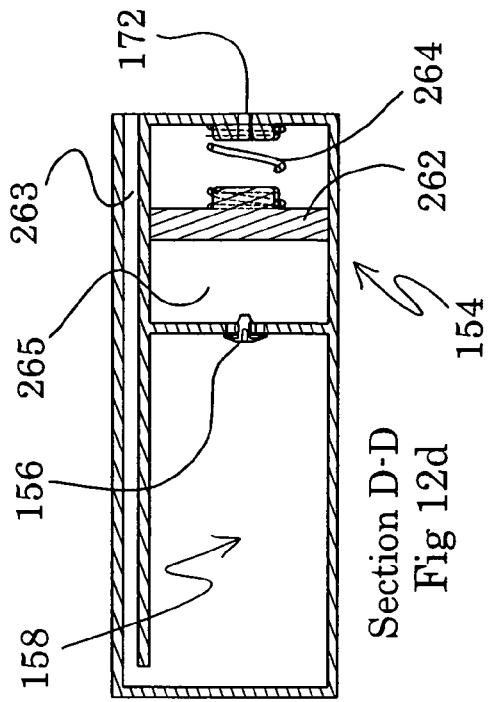
FIG. 12d is another sectional view of the accumulator.
Figure 12C:
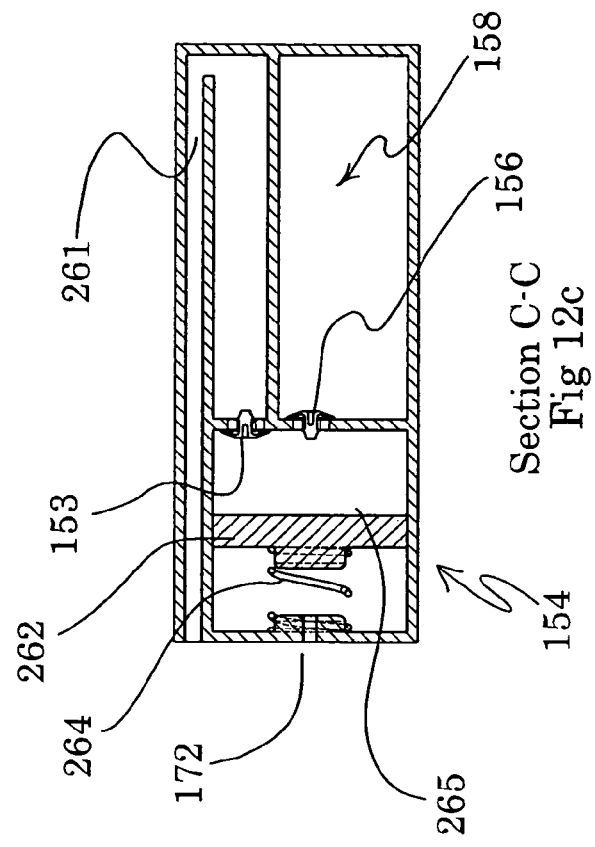
FIG. 12c is a sectional view of the accumulator.
Figure 12A:
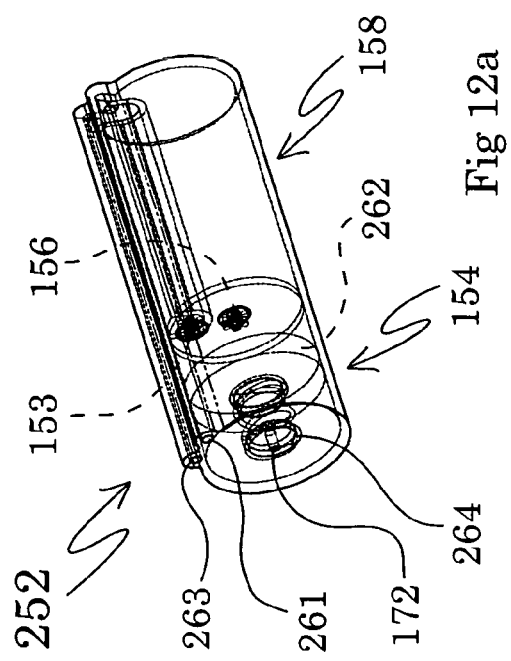
FIG. 12a is a perspective view of an accumulator.
Figure 12B:
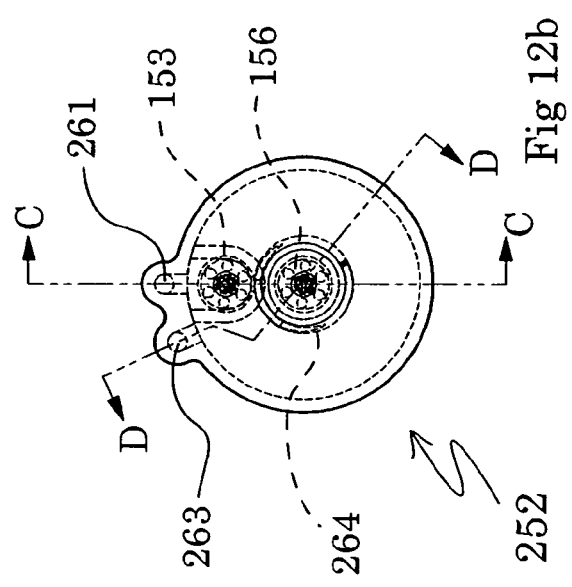
FIG. 12b is a top view of the accumulator.

FIGS. 12a-12d are various views of components contained inside of reservoir module 110. FIG. 12a is a perspective view of accumulator 252. FIG. 12b is a top view of accumulator 12b. FIGS. 12c and 12d are sectional views corresponding to the section lines in 12b. Contained within reservoir module 110 is oxygen accumulator 252 (comprising reservoir 158, check valves 153 and 156, and product control pump 154), inlet port 261, and outlet port 263. Accumulator 252 receives separated product gas through inlet port 261. Product inlet line 174 (shown in FIG. 10) is connected to inlet port 261 and links product control pump 154 to separation cartridge 206 through main valve 140 to transport oxygen rich gas separated by cartridge 206. Inlet port 261 connects to check valve 153 which allows product gas into product control pump 154.

Product control pump 154 includes piston 262, actuated by spring 264 within pump chamber 265, which pushes separated oxygen-rich product gas into reservoir 158. Check valve 156 opens to allow oxygen into the reservoir 158 and closes to prevent back flow of oxygen-rich gas when the desired pressure in reservoir 158 is attained. The low pressure of reservoir 158 exerts a force on check valve 156 to keep valve 156 closed. Reservoir 158 takes oxygen-rich gas produced by oxygen concentrator 100 and stores it at a low pressure above ambient until the product is required for use by patient P.

Product control pump 154 is driven by vacuum. Product control pump vacuum line 174 is connected to the vacuum drawn by vacuum pump 144 through main valve 140. When a vacuum is drawn, the force draws piston 262 down to compress spring 264 which expands pump chamber 265, and causes check valve 153 to open. Oxygen-rich gas from separation cartridge 206 flows through check valve 153 and enters pump chamber 265 in the volume created by the displacement of piston 262. At the appropriate time in the cycle, valve 140 will interrupt the vacuum to product control pump 154, and spring 264 will force piston 262 upwards. The movement of piston 262 will force oxygen rich gas in pump chamber 265 through check valve 156 and into reservoir 158. At the same time, check valve 153 closes to prevent more gas from entering pump 154. With this embodiment, no additional drive (other than the vacuum to pull piston 262 down and the spring force to move it up) is required for product control pump 154 which adds to the overall efficiency of the system.

In one embodiment, reservoir 158 has a capacity that is about four times larger than the size of the largest pulse provided by oxygen concentrator 100. In one embodiment, extra volume is included to account for separated oxygen used as a back flow in adsorbent columns 130a-130c. Specifically, main storage reservoir 158 for oxygen concentrator 100 can be designed according to the flow rates listed in Table 1. Storage reservoir 158 is 100 cc (cubic centimeters) to 400 cc in volume. Main storage reservoir 158 is maintained at a low pressure to provide delivery of the product gas to patient P through outlet 263 which is connected to final product dispensing line 202. In one embodiment, the pressure is between 1 atm (ambient) and 1.5 atm. Also acceptable are pressures less than eight psi (55,158 Pa), with a pressure of two and one half to five psi (17,236 to 34,473 Pa) preferred. The low pressure of reservoir 158 allows oxygen concentrator 100 to be used in most areas where high pressure oxygen is banned. Also, low pressure requires less energy to fill reservoir 158, which adds to the efficiency of the system by requiring a simpler pressurizing mechanism compared to high pressure systems.

Reservoir 158 contains pressure sensor 159 (such as a piezoresistive or capacitive sensor) that sends reservoir pressure signal 188 to ECM 148 (see FIG. 5). ECM 148 adjusts the speed of the motor of drive 146 based on reservoir pressure signal 188 in combination with the current settings on user interface 114. As patient P's respiratory rate increases for the current setting, more oxygen-rich gas from reservoir 158 is dispensed thus lowering the pressure of reservoir 158. The drop in pressure is sensed and the system will react by increasing the production of product gas. Similarly, a decrease in the respiratory rate of patient P at the current setting of oxygen concentrator 100 raises the pressure in reservoir 158. The rise in pressure is sensed and ECM 148 adjusts drive 146 accordingly to maintain a preset pressure range in reservoir 158. Thus, only the amount of oxygen used by patient P is produced by oxygen concentrator 100.

Figure 13:
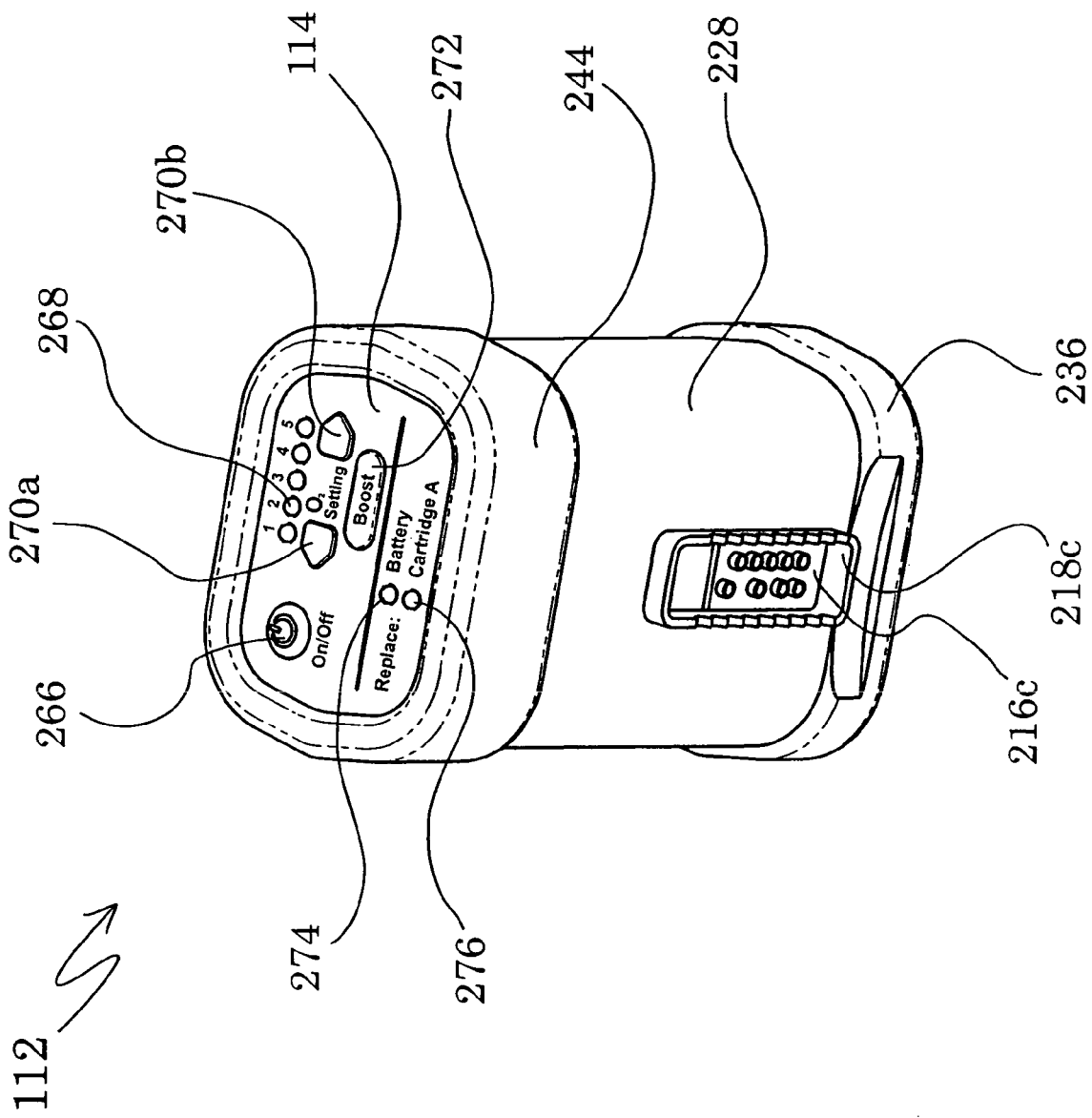
FIG. 13 is a perspective view of a control module.

FIG. 13 is a perspective view of the control module 112. Illustrated are the case 228 containing aperture 216c and socket 218c, and padding 236 and 234. Control module 112 contains user interface 114 comprising power switch 266, flow level indicator lights 268, flow setting switches 270a and 270b, boost switch 272, and indicator lights 274 and 276. Power switch 266 is an ordinary toggle or push button switch capable of turning oxygen concentrator 100 on and off.

Flow settings are dually controlled by patient P utilizing flow setting switches 270. First, continuous or pulse mode is selected by patient P. In a continuous flow mode, oxygen is dispensed at a continuous flow rate such as one to one and a half liters per minute. If oxygen concentrator 100 is set in a pulse mode for controlling flow, oxygen concentrator 100 utilizes dispensing valve 160 to provide pulse dispensing of product gas. The pulse mode is set to meet patient P's needs for the equivalent of one to five liters per minute of continuous oxygen flow. In one embodiment, a dial containing settings of one to five is utilized. In the embodiment illustrated in FIG. 13, flow setting switches are used to adjust the flow rate between various stepped levels. Each setting corresponds to the specific value for continuous flow, or a corresponding pulse volume. For example, settings for a pulse mode are contained in the table below.

TABLE 1

| Setting | Total Volume Pulse Range (cc/pulse) | Trigger Time (sec) | Pulse Flow Ramp Rate (sec) | Pulse Duration Max (sec) | Peak Pulse Flow (LPM) |
|---|---|---|---|---|---|
| 1 | 10 to 12 | .001 to .02 | .03 to .07 | .15 | 14 |
| 2 | 20 to 24 | .001 to .02 | .03 to .07 | .20 | 14 |
| 3 | 30 to 36 | .001 to .02 | .03 to .07 | .25 | 15 |
| 4 | 40 to 48 | .001 to .02 | .03 to .07 | .30 | 16 |
| 5 | 50 to 60 | .001 to .02 | .03 to .07 | .35 | 17 |

When the unit is set in pulse mode, product gas is dispensed only at the beginning of inhalation. In one embodiment, product dispensing valve 160 is only opened between zero and 0.4 seconds of the beginning of a breath of patient P. This controls the amount of oxygen removed from reservoir 158. In another embodiment, oxygen concentrator 100 is shut off if no pressure drop is sensed by nasal pressure sensor 190 for a set amount of time, such as two minutes, which in turn closes dispensing valve 160.

Patient P can temporarily increase (or "boost") the flow rate of oxygen by actuating boost control switch 272 on user interface 114. When boost switch 272 is activated, oxygen concentrator 100 increases the flow rate of oxygen for a set period of time, such as 10 minutes. After timing out, oxygen concentrator 100 returns to the previous setting. The boost function will not work if oxygen concentrator 100 is already operating at the maximum flow rate.

Indicator light 274 indicates power pack 108 is running low. Indicator light 276 indicates that there is a problem with separation cartridge 206, such as a bad connection with receptacle 208. In one embodiment, oxygen concentrator 100 contains three different colored lights: red, yellow, and green. The green light indicates that there are no problems detected with oxygen concentrator 100. A yellow flashing light or a yellow non-flashing light indicates a condition has been sensed that should be addressed. An example of such a condition is a low battery. A red flashing light indicates that a condition has been detected that requires an immediate response. A red non-flashing light indicates that oxygen concentrator 100 has failed, and has shut down. For example, if oxygen concentrator 100 fails to produce a stream of separated gas of eighty-five percent oxygen, oxygen concentrator 100 will detect this problem via breakthrough flow sensor 150. ECM 148 shuts off main valve 140 so no ambient air 162 is being submitted to the gas separation cartridge 206. Product gas is no longer being supplied to reservoir 158. After a few breaths, reservoir 158 will empty, triggering reservoir pressure sensor output 188 (shown in FIG. 5), which communicates to ECM 148 to shut down oxygen concentrator 100, and display the red warning light. This signals patient P that maintenance is needed. In addition to the aforementioned indicator lights, the unit may also contain a boost indicator light to indicate when a boost function is in operation. Similarly, an audible alarm may be included in oxygen concentrator 100 to indicate failure.

Figure 14:
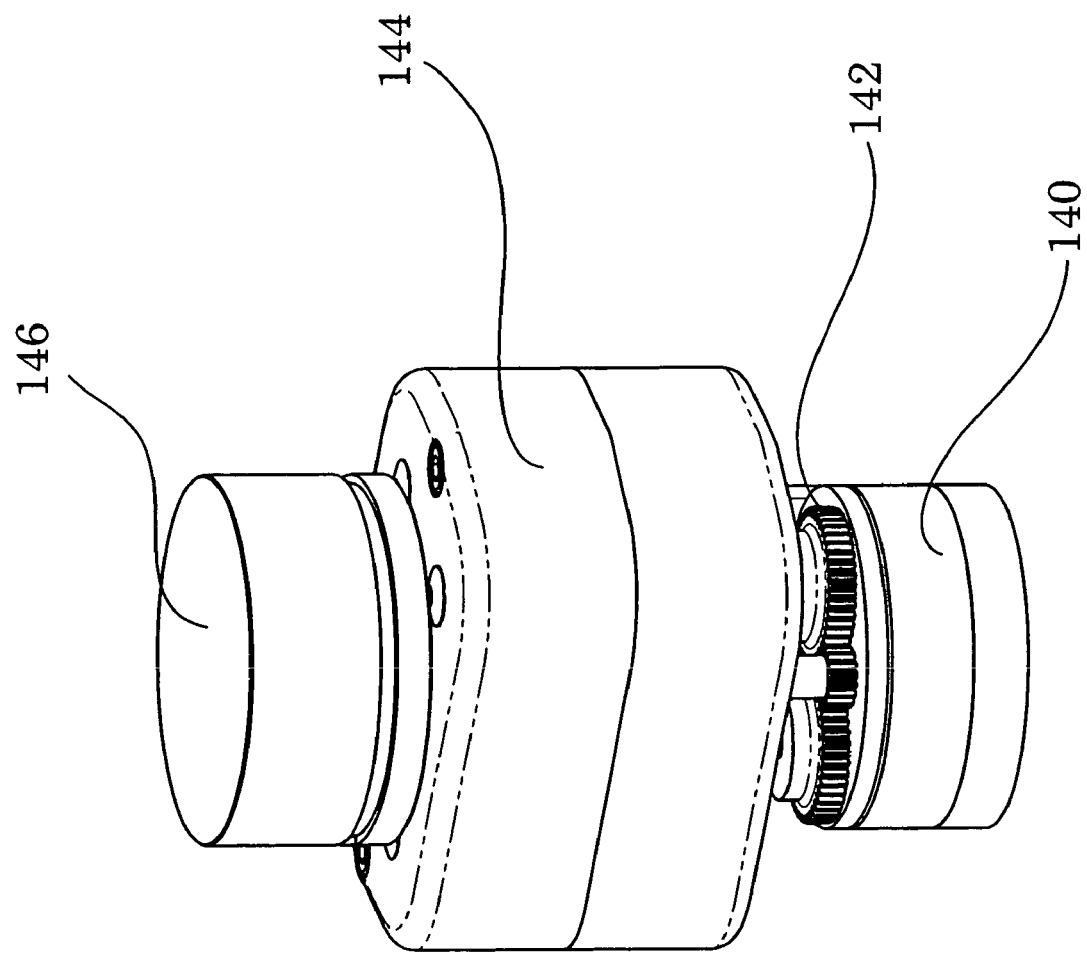
FIG. 14 is a front view of the interior components of the control module.

FIG. 14 is a front view of the interior components of control module 112. Illustrated are drive 146, vacuum pump 144, drive speed reducer 142, and valve 140. Drive 146 includes a DC motor, driven by battery power pack 108, which supplies the necessary power to operate vacuum pump 144. The motor draws a maximum of 15 watts of power. Vacuum pump 144 is a positive displacement pump. In this embodiment, drive 146 runs both vacuum pump 144 and valve 140. Vacuum pump 144 is run by the motor at one speed, while valve 140 is run off the same motor but at a reduced speed. The reduction in speed is accomplished with gears that comprise drive speed reducer 142 between the motor of drive 146 and valve 140.

Valve 140 is a valve containing a minimum number of ports equal to two times the number of adsorbent beds (columns) in separation cartridge 206. Additionally, main valve 140 contains other ports for the inlet of ambient air 162, vacuum provided by vacuum pump 144, and recycling of product gas used to purge columns 130a-130c during repressurization. In the preferred embodiment, valve 140 is a rotary valve, but may also be a solenoid valve, directional control valve, or series of individual valves in communication with each other and each connected to an adsorbent column 130a-130c.

In an alternate embodiment, drive 146 may contain an independent motor for operating valve 140. If valve 140 is run by an independent motor, that motor is powered by power pack 108 and synchronized with the other motor(s) of drive 146 by ECM 148. As illustrated, drive 146 contains a single motor and valve 140 is connected to a system of gears that comprise drive speed reducer 142. Alternately, drive speed reducer 142 can be any common power transmission components such as pulley and belts, or gears and sprockets.

Figure 15:
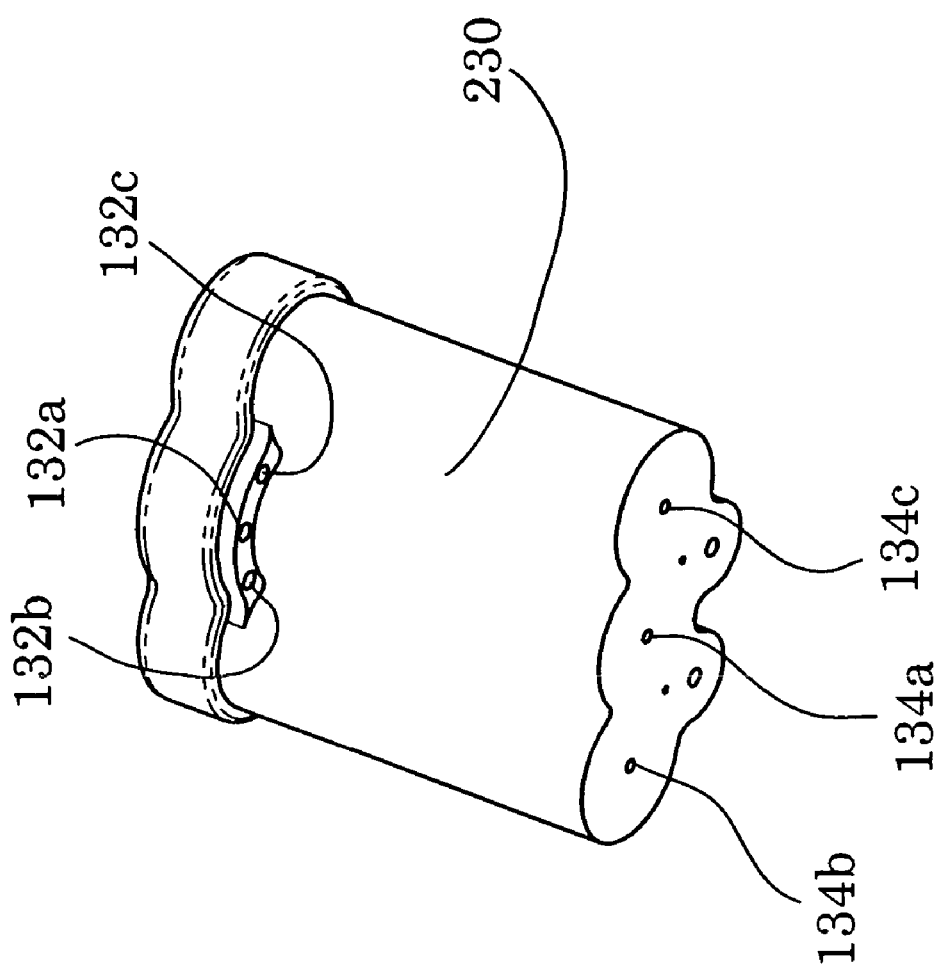
FIG. 15 is a perspective view of the cartridge contained within a cartridge module.

FIG. 15 is a perspective view of separation cartridge 206 contained within separation cartridge module 116. Illustrated are inlet ports 132a-132c, outlet ports 134a-134c, and casing 230. In the embodiment illustrated, three adsorption columns are contained within casing 230 with one inlet port 132a-132c, and one outlet port 134a-134c, for each adsorption column 130a-130c. Each adsorption column 130a-130c is a hermetically sealed container containing a bed of adsorption material, preferably a zeolite capable of adsorbing nitrogen gas, such as lithium low silica 13X zeolite. Each bed contains between five and twenty-five cubic centimeters of material, and in one embodiment contains fifteen (plus or minus one) cubic centimeters of material. The adsorbent bead size is a thirty by sixty mesh, wherein thirty mesh is equal to 0.0234 inches (0.0594 cm) and sixty mesh is equal to 0.01 inches (0.0254 cm).

Column inlet ports 132a-134c are connected to receive either ambient air 162 or vacuum, while outlet ports 134a-134c expel product gas or receive purge gas. This arrangement promotes ordering of gases within the columns 130a-130c by having oxygen rich gas always present at one end of the column. This results in improved efficiency as air flow through the columns 130a-130c creates an oxygen rich zone continuously at one end, which allows the vacuum to evacuate and desorb the previously adsorbed nitrogen where it is contained in the greatest concentration.

Figure 16:
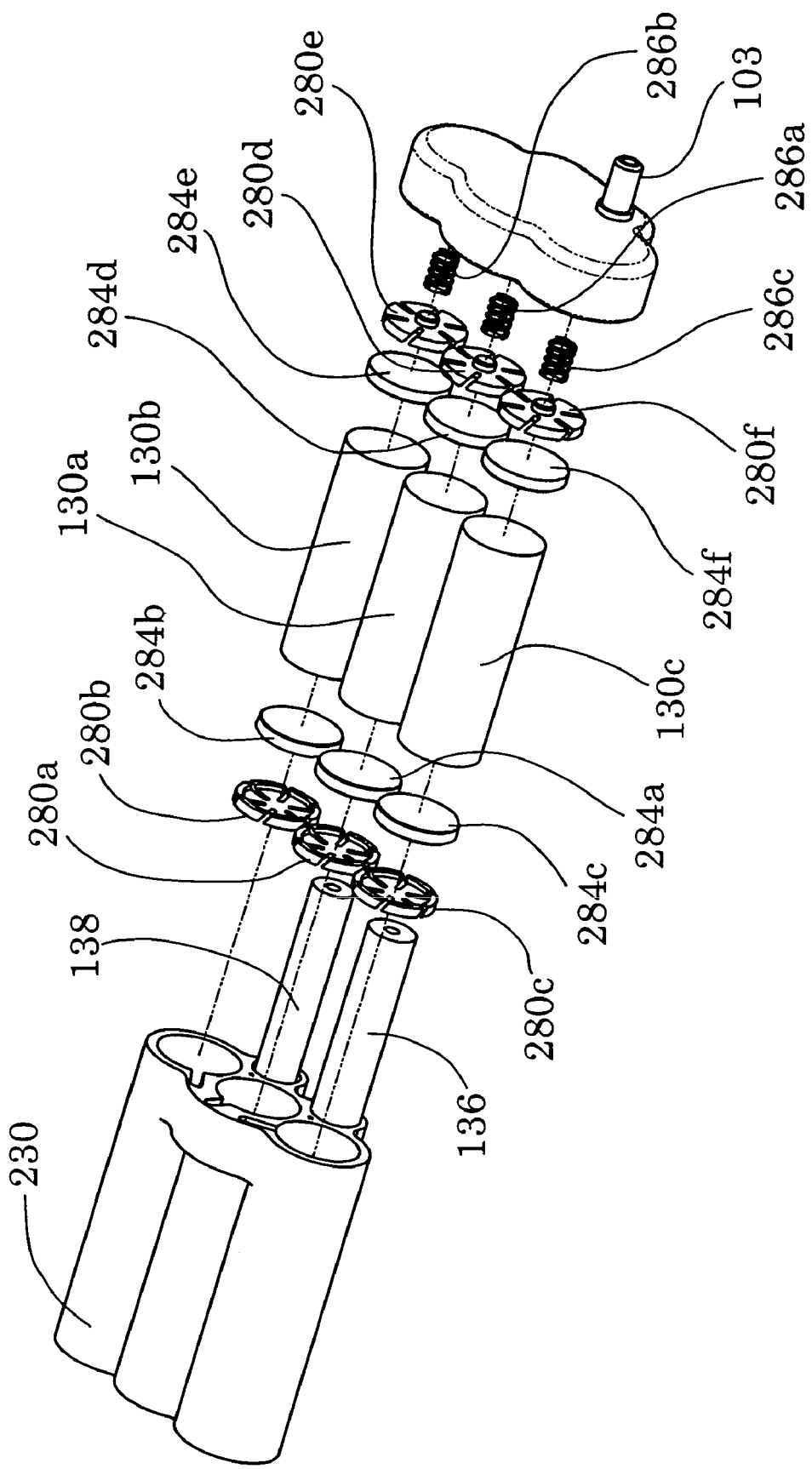
FIG. 16 is an exploded view of columns and filters within the cartridge.

FIG. 16 is a perspective view of the columns 130a-130c and the filters 136 and 138 within casing 230 of separation cartridge 206. Illustrated are final product filter 138 connected to product gas outlet port 103 which connects to tubing 102, inlet air filter 136, and adsorbent columns 130a-130c each comprising spin inducers 280a-280f, adsorbent material 282a-282c, porous filters 284a-284f, and springs 286a-286c.

Springs 286a-286c are coil springs that hold each adsorbent column in compression 130a-130c in place within casing 230 of separation cartridge 206 to prevent movement of adsorbent beads. Spin inducers 280a-280f help force even distribution of gases through columns 130a-130c, which helps to keep the MTZ well defined for more accurate detection.

Adsorbent material 282a-282c is the same as that previously described. Filters 136 and 138 are constructed of common filtering materials and are used to remove dust and other large particulate matter from the air streams to assure that the flow of oxygen out to patient P is free of such materials. Porous filters 284a-284f are a small section of material commonly used as a particle filter provided at each end of columns 130a-130c. Porous filters 284a-284 fact to prevent adsorbent particles from contacting the mechanisms and valving of concentrator 100.

Figure 17:
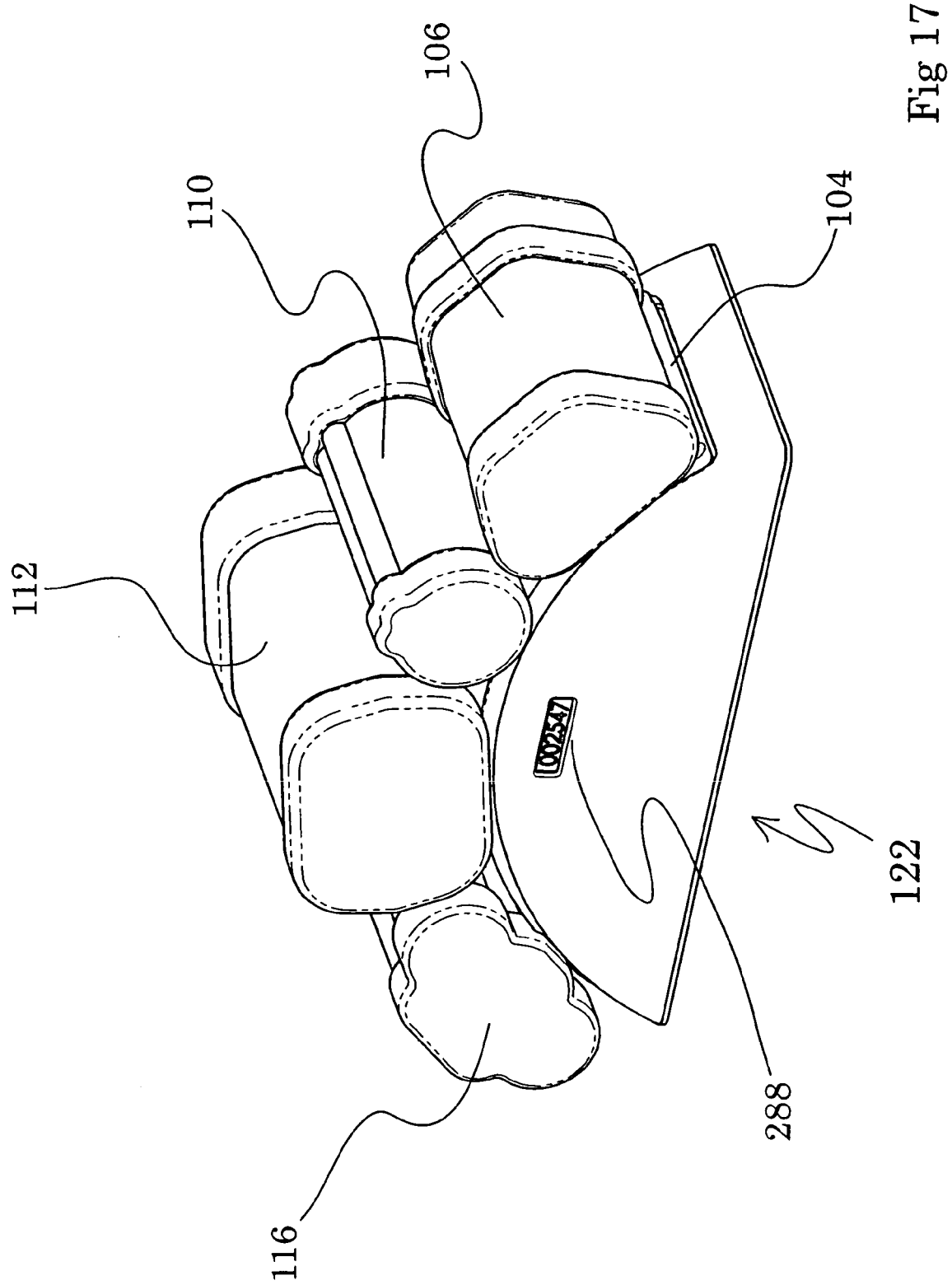
FIG. 17 is a rear perspective view of the oxygen concentrator and the docking station.
Figure 18:
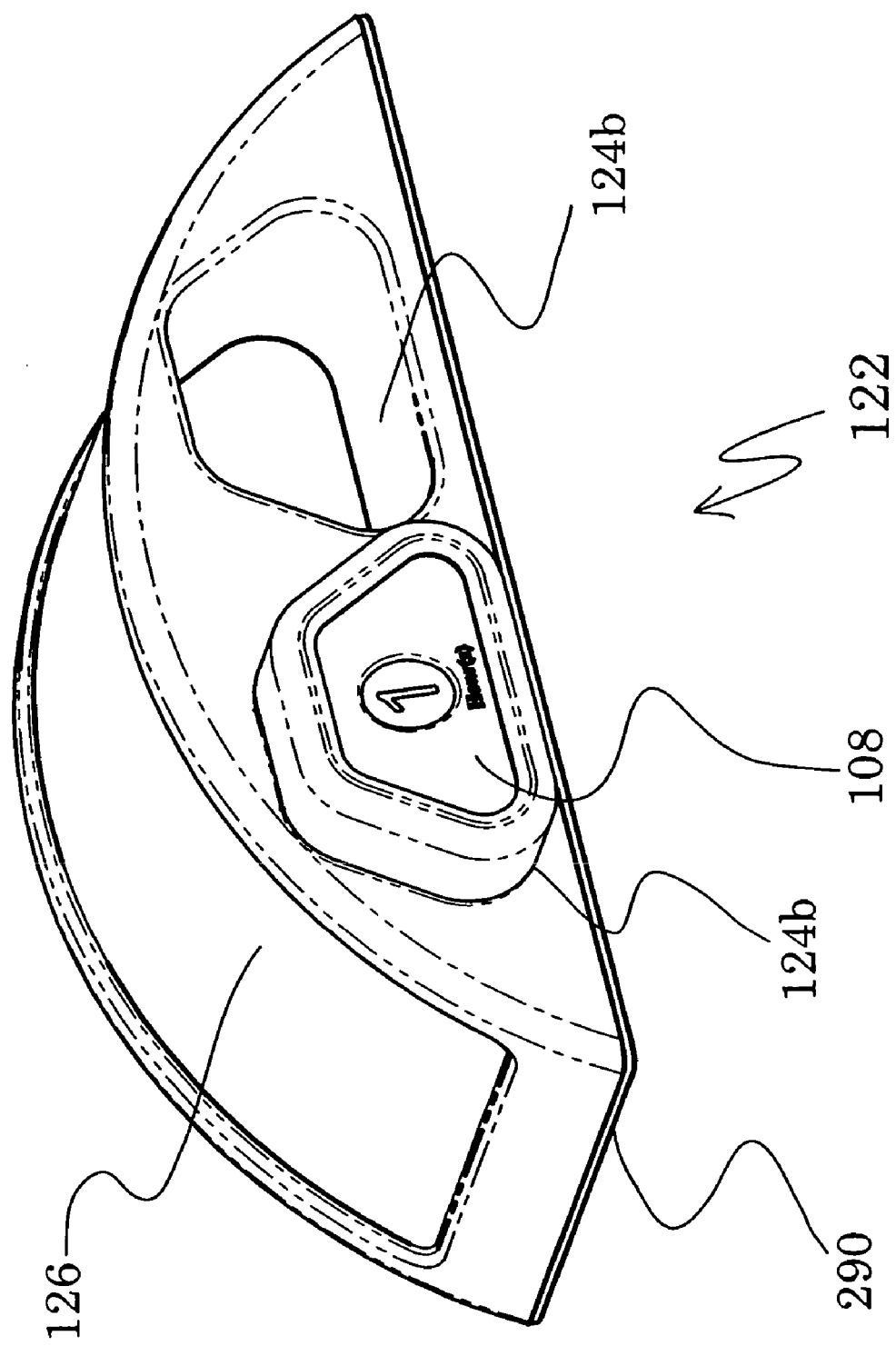
FIG. 18 is a front perspective view of the docking station.

Docking Station 122 (FIGS. 17-18)

FIG. 17 is a perspective view of the back side of oxygen concentrator 100 on docking station 122. Illustrated are oxygen concentrator 100 comprising power module 106, reservoir module 110, control module 112, and separation cartridge module 116, belt 104, and docking station 122 containing status display 288. Status display 288 is an LED, LCD, or similar digital display used to provide information to patient P such as time of day, time the concentrator has been used, time of recharging for power pack 108, or similar information. Additionally, docking station 122 may contain other controls (not illustrated) including a boost setting while the concentrator is docked, a mode switch for switching between pulse and continuous flow of oxygen, and indicator lights to show expected battery life, adsorbent column life, gas input, gas output, or gas separation system malfunctions, or other similar items that were previously described as part of user interface 114.

FIG. 18 is a perspective view of the docking station 122 with oxygen concentrator 100 removed. Concentrator dock 126 is visible on docking station 122 with oxygen concentrator 100 removed. Concentrator dock 126 may optionally contain electrical connections (not illustrated) to charge power pack 108 contained within power module 106 while oxygen concentrator 100 is docked. Additionally, docking station 122 contains a power cord (not illustrated) available to connect to a wall socket or other power source such as a car utility plug. Docking station 122 uses power provided through the power cord to operate oxygen concentrator 100 and/or recharge power packs 108. Docking station 122 contains a flat bottom 290 to rest on a level surface and allow oxygen concentrator 100 to be in the docking station without moving. Alternately, docking station 122 is mountable to a wall in one embodiment, and is a free standing device that is set on a generally flat surface in another embodiment.

In one embodiment, docking station 122 comprises indicator lights and control power switch (not illustrated) in addition to status display 288, power pack chargers 124a and 124b, and concentrator dock 126. Indicator lights provide information to patient P utilizing oxygen concentrator 100. Indicator lights will indicate if oxygen concentrator 100 is functioning properly, requires maintenance, or has failed. Control switch is a master switch for supplying or terminating power or controlling the setting of flow for oxygen concentrator 100. Status display 128 is an LED, LCD or similar digital display that can be used to indicate various information to patient P such as time of day, time oxygen concentrator 100 has been docked, time of recharging for the power pack, or similar information.

Docking station 122 also contains power pack chargers 124a and 124b and concentrator dock 126. Docking station 122 contains a power cord (not illustrated) available to plug into a wall socket or a similar power pack. Docking station 122 converts AC power to recharge power pack 108 in power pack chargers 124a and 124b. Power pack chargers 124a and 124b contain contacts that are used to transfer power to power pack 108 while recharging. Alternatively, a power pack 108 placed in charger 124a or 124b is inductively coupled to recharge the power pack 108. Similarly, power is provided to oxygen concentrator 100 itself while on docking station 122, and to recharge of the power pack 108 (see FIG. 4) still attached to the oxygen concentrator 100. Concentrator dock 126 is shaped to provide a place to set oxygen concentrator 100 while docked, as well as facilitate easy removal of oxygen concentrator 100 for ambulatory use.

In one embodiment, docking station 122 performs several functions with oxygen concentrator 100 docked. First, oxygen concentrator 100 is allowed to run without utilizing power pack 108 while it is docked. Second, a boost setting is available to increase the delivery rate of oxygen while oxygen concentrator 100 is docked. Boost switch 272 is located on user interface 114 (See FIG. 13). In an alternate embodiment, a boost switch is located on docking station 122. Upon removal of oxygen concentrator 100 from docking station 122, the boost setting is removed and oxygen concentrator 100 operates at a set delivery rate in either a continuous or pulse mode.

Oxygen concentrator 100 contains flow setting switch 270 (FIG. 13), and a mode switch (not illustrated). The mode switch allows patient P to select continuous or pulse flow. In one embodiment, patient P is allowed to adjust the setting of oxygen concentrator 100 only while docked. That is, patient P can reprogram by changing a pulse setting (e.g., from 2 to 3), or continuous flow mode (e.g., from 1.0 to 1.5 liters per minute), only while oxygen concentrator 100 is on docking station 122. Patient P wishing to adjust settings will be required to hold the control switch while adjusting the flow setting dial or mode switch. In another embodiment, docking station 122 contains a switch automatically activated by placing oxygen concentrator 100 in docking station 122 which allows patient P to adjust flow setting. The requirement that settings can only be changed during docking prevents accidental switching of the flow mode of oxygen concentrator 100 during ambulatory use. For example, there is no change in flow if flow setting switch 130 is bumped, which would normally increase oxygen flow. If oxygen concentrator 100 can only be reprogrammed in docking station 122, oxygen concentrator 100 will remain in the preset mode set at docking station 122 and will not increase or decrease flow by a change of the setting. In one embodiment, the flow setting switch and mode switch are located on a user interface located directly on docking station 122.

Another function of docking station 122 is to provide diagnostic features of the system. Docking station 122 may indicate expected battery life, adsorbent column life, or pump malfunctions through the use of indicator lights, or status display 128, or a combination of both. Alternatively, these items are located on user interface 114, or at a combination of locations of user interface 114 and docking station 122. For example, battery life indicator 142 is located directly on power pack 108 that comprises the battery itself, and battery problem warning light 274 is on user interface 114 also. Similarly, adsorbent cartridge warning light 276 is located on user interface 114, but may also be on either the cartridge module 116 or docking station 122 as well.

Concentrator Efficiency

Oxygen concentrator 100 can produce a stream of product gas containing a range of 85-95 percent oxygen which provides up to 5 liters per minute pulsed equivalent of product gas. By utilizing vacuum swing adsorption, the separation process phases are all performed at less than 1 atm.

Utilizing a vacuum to exhaust unwanted gas from adsorbent columns 130a-130c improves efficiency of the oxygen concentrator 100. Less power is required than pressure swing adsorption (PSA) or vacuum-pressure swing adsorption (VPSA), which results in a smaller battery and thus a lighter weight product. Oxygen concentrator 100 as disclosed weighs less than 3 pounds (1.4 kg) and occupies less than 1 liter of volume. Also, the efficiency of the system allows for oxygen concentrator 100 to operate for at least three hours while producing up to 5 liters per minute pulsed equivalent of product gas without requiring patient P to attend to the unit, e.g. changing the battery. Further, the low energy consumption causes less heat transfer. The product gas is discharged from the separation system at a temperature of ± six degrees Celsius from that of the ambient air. This eliminates the need for heat exchangers which add to the overall weight and reduces system efficiency. The amount of heat generated causes no discomfort to patient P wearing and utilizing the oxygen concentrator 100. Also, upon starting oxygen concentrator 100, the flow of product gas will increase from 21 percent oxygen (ambient) to 85 percent or more oxygen in under two minutes.

Improvements over the prior art are attained by regulating the device to only separate the amount of oxygen needed by patient P at any given time. The prior art separates a flow of oxygen and delivers that rate to patient P as a steady flow. Patient P is only inhaling this oxygen during about ⅓ of the normal breathing cycle. Within the inhalation portion of the breathing cycle, the volume of gas inhaled last stays in the dead space of the airways and is not presented to the alveoli. Therefore if oxygen is dispensed to patient P only during the early part of inhalation, less than ⅓ the steady flow is actually required. Moreover, prior art devices do not adjust the flow based on a patient P's needs, but operate at the same steady flow. The present concentrator slows down its entire cycle rate producing only the amount of oxygen needed. Thus, oxygen concentrator 100 retains a high oxygen recovery percentage at all product flow rates while minimizing energy consumption and maximizing adsorbent life. Patient P's actual needs vary with real time changes in activity. This causes a corresponding variation in breathing rate. Oxygen concentrator 100 tracks patient P's breathing rate and adjusts oxygen separation and delivery rates proportionally. In combination, these two features allow oxygen concentrator 100 to separate oxygen only at the rate it is being consumed, resulting in a reduction in the amount of oxygen needing to be separated for patient P.

Another improvement over the prior art involves reducing the waste of separated oxygen in the various adsorb and desorb cycle phases. This is typically referred to as maximizing product recovery. The primary system components become larger or smaller as the amount of oxygen separated increases or decreases. Therefore, a dramatic reduction in size and weight of the concentrator requires use of as much separated oxygen as possible by delivering it to patient P rather than losing it to the waste stream. The prior art works by using the Skarstrom cycle well known to those skilled in the art.

During one phase of the Skarstrom cycle in PSA or VPSA, air is pumped into one end of a column of adsorbent pressurizing it above atmospheric pressure while oxygen is flowing out of the opposing end. Nitrogen is being adsorbed as the MTZ propagates toward the oxygen outlet end of the column. This phase is terminated before the MTZ breaks through into the oxygen stream so that oxygen purity is not diluted by the nitrogen rich air trailing the MTZ. If it is terminated earlier than necessary to maintain purity there will be substantial separated oxygen left in the column in front of the MTZ that is not passed to the patient. During the next cycle phase the column pressure is reduced to a lower cycle pressure desorbing the nitrogen that was adsorbed during the separation phase and it is passed to the waste stream. Some of the oxygen left in the column at higher pressure will also be passed to the waste stream as gas flows from the column when pressure is reduced. Recovery of separated oxygen can therefore be maximized by stopping the previous separation phase just short of breakthrough, leaving minimal oxygen in the column to be lost to the waste stream during the reduced pressure evacuation phase. The position of the MTZ needs to be accurately known to terminate the separation phase for optimal recovery without compromising purity. This position cannot be accurately estimated because its propagation rate is a function of many variables including product oxygen flow rate, high and low cycle pressures, temperature, adsorbent water content and the amount of other contaminants accumulated in the adsorbent. Prior art systems stop the separation phase well short of breakthrough to encompass worst case operating conditions without sacrificing purity and thereby waste separated oxygen in the evacuation phases during most typical non-worst case operating conditions.

Oxygen concentrator 100 determines the position of the MTZ just prior to breakthrough and terminates the flow from outlet 134 for the remainder of the feed phase or adjusts the motor speed, as previously described. Additional oxygen is left in the column at the end of a feed phase and is wasted during the evacuation phases. This is oxygen adsorbed by the adsorbent combined with oxygen present in the interstitial and dead spaces of the adsorbent and column. All adsorbents used in oxygen separators adsorb nitrogen, and also oxygen to some extent. The adsorbent used in oxygen concentrator 100 presents a very high ratio of adsorbed nitrogen to adsorbed oxygen. As the amount of oxygen adsorbed is minimized through the choice of an adsorbent with a low affinity for oxygen, the amount of adsorbent needed to separate a given amount of nitrogen during a separation phase will decrease as its affinity for nitrogen increases. The less adsorbent needed to adsorb a given amount of nitrogen, the less adsorbent there is to adsorb oxygen and the smaller the column can be with less interstitial and dead space.

For example, a LiLSX adsorbent referred to as Oxysiv MDX from UOP Corporation has a very high ratio of adsorbed nitrogen to adsorbed oxygen in the operating pressure range of oxygen concentrator 100. The Skarstrom cycle of the prior art uses a purge phase in which separated oxygen is fed back into the product end of the column while nitrogen rich gas is passing out of the opposing end of the column into the waste stream as the pressure transitions to the lower cycle pressure. While this purge can enhance product purity, some of the purge oxygen passes all the way through the column and is lost to the waste stream. Oxygen concentrator 100 using VSA achieves a measured 60% oxygen recovery rate, compared to a typical recovery rate of 30% for the prior art utilizing PSA.

Another improvement over the prior art concerns the choice of adsorbent and operating pressure range. The energy required by the separation process directly defines the weight and size of major components such as the battery, motor and gas pump of a concentrator. Minimizing the amount of adsorbent minimizes the amount of energy needed to separate a given amount of oxygen. Each adsorbent has a characteristic pair of isotherms that show the amount of oxygen and nitrogen a given mass of adsorbent will hold at equilibrium over a range of pressures and vacuums for these gasses at a constant temperature. The cycle phases of the system necessarily include the pumping of gas contained in volumes of adsorbent to produce a change in nitrogen partial pressure between a chosen higher pressure and a chosen lower pressure. The pneumatic energy a pump must deliver in the process of cycling a given volume of gas between a higher and a lower level is in direct proportion to the volume of gas pumped multiplied by the difference between the high and low vacuum levels. The isotherms for various adsorbent candidates specify the amount of nitrogen contained in a fixed mass of adsorbent at a fixed temperature as a function of nitrogen partial pressure.

Figure 19:
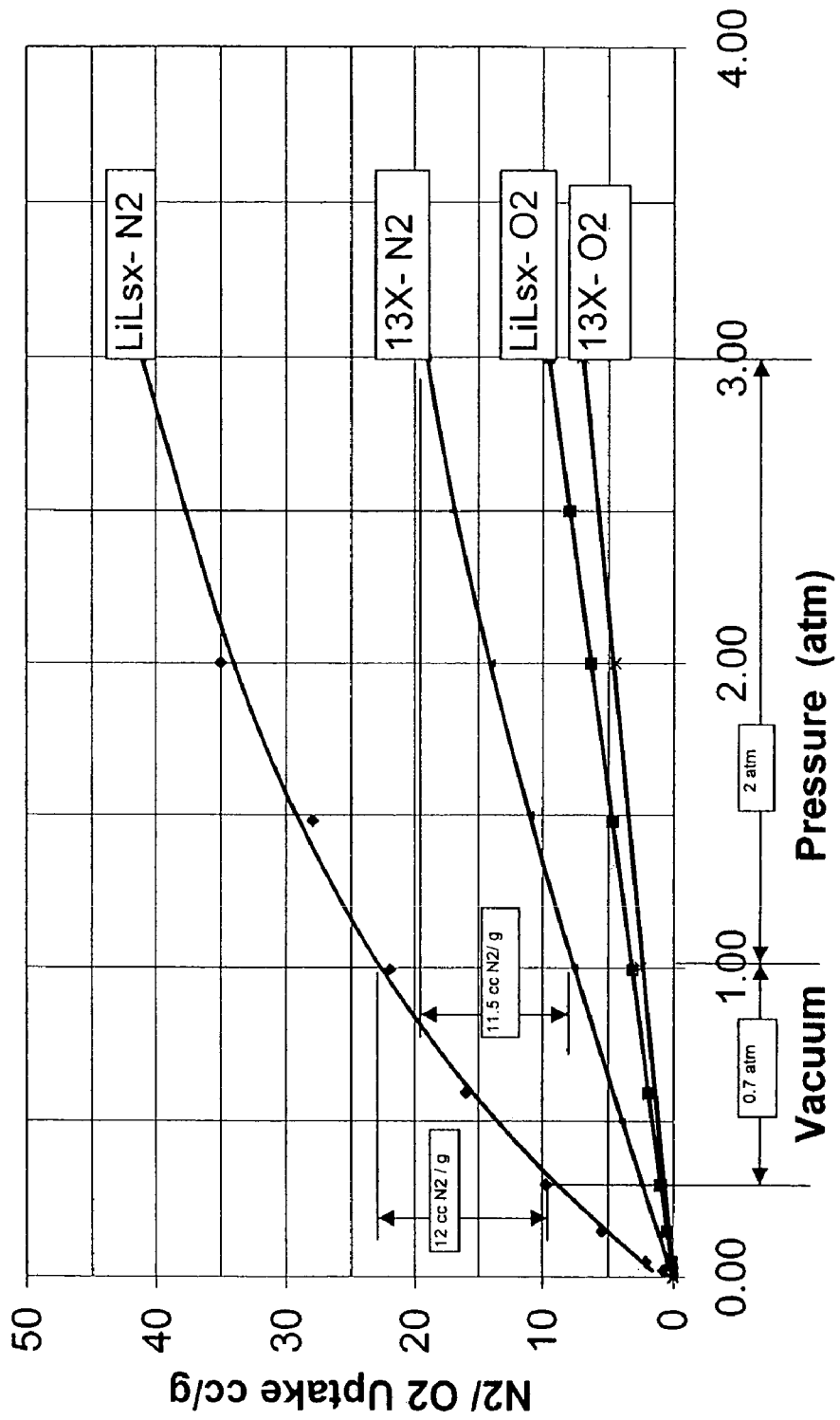
FIG. 19 is a chart showing the adsorption isotherms for two different adsorbent materials.

An example of the isotherm for the LiLSX adsorbent Oxysiv MDX along with the isotherm for a typical 13X type adsorbent used in the prior art is shown in FIG. 19. Having minimized the amount of oxygen needed to be separated from air and having maximized the recovery percent of oxygen as previously disclosed, along with knowing the percentage of oxygen present in air prescribes a specific minimum amount of air that must be moved into the system to produce the needed oxygen. This minimum amount of air minus the maximized separated oxygen must pass out of the system as a minimized volume of waste gas. Oxygen concentrator 100 acts to minimize the flow rates of the air feed stream and the waste stream. This flow must be pumped across a pressure difference defined by the choice of high and low operating pressures requiring a pumping energy that is proportional to both the flow rate and the pressure difference. The gas streams are pumped into or out of the adsorbent during each complete cycle to produce the needed swing in pressure between high and low cycle pressure levels allowing the separation of nitrogen from oxygen. Minimizing the amount of gas being pumped through the system reduces the pumping energy in proportion to reductions in the difference between chosen high and low pressure points that the gas must be pumped across. The isotherm for nitrogen shows that nitrogen is transferred in or out of the adsorbent with the smallest change in pressure where the slope of the isotherm is the steepest. Using typical PSA, a ratio of high to low pressure levels in these systems needs to be 3:1 or greater to maintain the desired oxygen purity. Lower pressure ranges, i.e. sub-atmospheric or vacuum ranges used in VSA, allow this ratio to be maintained with less total difference between the high and low pressure levels.

For example, prior art operates between 1 and 3 atmospheres for a 3:1 ratio and a pressure difference between high and low levels of 2 atmospheres. Oxygen concentrator 100 using VSA operates between 0.3 atmospheres and 1 atmosphere. A ratio of about 3.3:1 is achieved with a pressure difference of only 0.7 atmospheres. Operating on this range of the isotherm as seen in FIG. 19 allows just as much nitrogen to be passed in and out of the LiLSX adsorbent with a 0.7 atmosphere pressure range as a PSA system does with 13X adsorbent and a 2.0 atmosphere pressure range. The LiLSX adsorbent allows a cycle pressure range that is nearly ⅓ that of a PSA system with a proportional reduction in pumping energy.

Oxygen concentrator 100 is a quiet device. When oxygen concentrator 100 is running, it produces a noise level in the range often to thirty decibels. Further, with the compact size of the parts, vacuum pump 144 is running continuously and there is very little vibration to affect a person using it docked or wearing it as an ambulatory device. The device of the present invention with the described components weighs less than three pounds (1.36 kg). The compact size (less than about 61 cu. in. (1000 cc)) allows for easy portability. Similarly, the small size does not disrupt counter space or storage when used at home. The device does give off some heat, however the outer case is less than 6 degrees Celsius higher than ambient when oxygen concentrator 100 is running on battery power. The device may emit more heat while it is docked and operating on AC power to charge the power pack 108, but is still less than 15 degrees Celsius above ambient.

Based on the foregoing embodiments, the efficiency of the concentrator can be determined. One measure of efficiency is the ratio of oxygen produced to the amount of adsorbent material used to obtain the oxygen, represented by the following:

Qp=Liter/min $O_2$ produced

Madsorbent=Kg of Adsorbent Material for example, the disclosed embodiments include adsorbent columns 130a-130c, with each column containing 15 cubic centimeters (cc) of adsorbent material with a density of 0.66 gm/cc. That is:

$$(3 \text{columns})\left(\frac{15 \text{ cc}}{\text{column}}\right)\left(\frac{0.66 \text{ gm}}{\text{cc}}\right) = 30 \text{ gms for the system.}$$

The following flow rates (Qp) were obtained by the above disclosed concentrator:

Qp max=1.5 L/min

Qp min=0.14 L/min

This results in a range for kilograms of adsorbent material to oxygen flow rate of:

$$0.020 < \frac{Madsorbent}{Qp} < 0.214$$

Similarly, flow rates (Qp) were determined for a system that contains three adsorption columns, each column containing 15 cc of adsorbent material. The separation completed in a range of 0.3 atm to 0.95 atm. Values were calculated for breakthrough time, work, battery life, and flow rate. The volume of gas contained in a column at the end of a feed phase was 150 cc. These constants were used to determine the following measures of efficiency:

Work per evacuation cycle or pneumatic power requirements were determined based on the following calculations:

i W(work)=(volume moved)*(vacuum differences);

The vacuum differences are calculated as the vacuum pump is continuously changing gas out, and as vacuum progresses to end point. From this:

$V_H$=Vacuum upper level $V_L$=Vacuum lower level

Vol=Volume of gas in the column at end of feed phase $W = Vol^*(V_H - V_L)^*(1 + (V_H/(V_H - V_L))^* \ln(V_L/V_H) + \ln(V_H/V_L))$ Inserting the above constants and converting to joules (multiply by 100.32 to get L*atm to joules) yields:

W=4.81 joules

Thus, 4.81 joules is required to evacuate the gas which desorbs during the evacuation phase. From experimentation, the following flow rates (LPM is liters per minute) and cycle times were recorded:

| | |
|---|---|
| Qp (flow rate) | Low = .14 LPM |
| | Med = .720 LPM |
| | High = 1.5 LPM |
| Cycle time | Low = 5.6 sec. |
| | Med = 1.12 sec. |
| | High = .54 sec. |

Power consumption can be determined by calculating work divided by the time of the cycle.

Low flow power=4.81 joule/5.6 sec=0.85 watts

Medium Flow power=4.81 joule/1.12 sec=4.29 watts

High flow power=4.81 joule/0.54 sec=8.9 watts

From the above, a measure of energy consumed to the flow rate can be made and used as an indicator of the system efficiency:

$$\text{Low: } \frac{.85 \text{ w}}{.14 \text{ LPM}} = 6.07 \text{ w/LPM}$$

$$\text{Medium: } \frac{4.29 \text{ w}}{.72 \text{ LPM}} = 5.95 \text{ w/LPM}$$

$$\text{High: } \frac{8.9 \text{ w}}{1.5 \text{ LPM}} = 5.93 \text{ w/LPM}$$

Another measure of efficiency is the ratio of mass of the power pack (Mpowerpack) compared to the amount of oxygen produced (Qp) over time:

$$\frac{Mpowerpack}{QpT(\text{time})}$$

The following constants are used in the calculation: the battery cell is a type 18650 lithium ion battery with 7.4 watts-hrs, measuring 42 g; motor efficiency is 90 percent; and vacuum pump efficiency is 80 percent.

$$\text{Pneumatic work} = 6 \text{ W/L/min. Thus,}$$

$$\text{Electric power} = \frac{6 \text{ W/LPM}}{(.9)(.8)} = 8.3 \text{ W/LPM}$$

Battery mass compared to energy consumption is:

$$\frac{42 \text{g}}{7.4 \text{ (watt)(hr)}} \left( \frac{1 \text{ Kg}}{1000 \text{ g}} \right) \frac{8.3 \text{ watt}}{\text{LPM}} = .047 \frac{\text{Kg}}{\text{LPM } (HR)}$$

Total battery mass for the power pack can be determined from this equation. For example, if a patient requires the concentrator to run for four hours at setting of "3" and takes 20 breaths per minute (the medium flow rate):

$$(4 \text{ hr}) * \frac{.047 \text{ kg}}{\text{LPM (hr)}} .72 \text{ LPM} = .135 \text{ kg}$$

The mass of the batteries needed is 0.135 Kg. Assuming each battery cell is 42 g as previously stated, the number of batteries for the power pack can be calculated:

$$.135 \text{ kg} \left( \frac{1000 \text{ g}}{1 \text{ kg}} \right) \frac{\text{battery cell}}{42 \text{ g}} = 3.2 \text{ battery cells}$$

Although the present invention has been described with reference to preferred embodiments, workers skilled in the art will recognize that changes may be made in form and detail without departing from the spirit and scope of the invention. For example, larger flow rates may be achieved by scaling the concentrator components to achieve desired flow rates at the disclosed efficiencies.

The invention claimed is:

1. A method of providing concentrated oxygen product gas to a patient, the method comprising:
producing product gas by a vacuum swing adsorption (VSA) process with an oxygen concentrator comprising a plurality of separation columns connected to a vacuum source driven by a motor, wherein the VSA process comprises:
(a) introducing ambient air at atmospheric pressure into a first end of a column containing an adsorbent material that preferentially adsorbs nitrogen and removes oxygen-rich product gas out a second end of the column;
(b) evacuating the column through the first end to remove adsorbed gas from the column;
(c) repressurizing the column by introducing ambient air into the first end of the column until pressure within the column is near 1.0 atm; and
(d) repeating steps (a)-(c);
pumping product gas separated by the concentrator to a product reservoir;
sensing the pressure of the product gas in the reservoir;
controlling the speed of the motor based on the sensed pressure in the reservoir to control a rate of which product gas is produced by the VSA process; and
delivering product gas to the patient.

2. The method of claim 1 and further comprising:
introducing product gas into the column through the second end during a portion of step (c).

3. The method of claim 2 wherein introducing product gas occurs during an initial portion of step (c).

4. The method of claim 1 and further comprising:
terminating step (a) based upon a position of a mass transfer zone to prevent breakthrough of nitrogen-rich gas out the second end of the column.

5. The method of claim 1 wherein delivering the product gas to the patient occurs during a portion of the patient's inhalation.

6. An oxygen concentrator comprising:
an oxygen reservoir;
a plurality of adsorbent columns, each having an inlet, an outlet and a bed of adsorbent material;
a vacuum pump for removing separated nitrogen rich gas from the column inlets;
a product control pump for pumping oxygen rich gas from the column outlets to the oxygen reservoir, wherein the product control pump is run by the vacuum pump;
a control valve for controlling flow of fluids in and out of the columns;

a motor for driving the vacuum pump and control valve to produce vacuum swing adsorption (VSA) cycles in which oxygen-rich product gas is separated and accumulated in the reservoir;

a pressure sensor for providing a signal as a function of gas pressure in the oxygen reservoir; and an electric control module (ECM) that receives a signal from the pressure sensor, and adjusts the speed of the motor based on the signal to control a rate at which oxygen rich gas is produced by the VSA cycles.

7. The oxygen concentrator of claim 6 wherein the oxygen concentrator has a volume of less than 1.0 liter.

8. The oxygen concentrator of claim 6 wherein the oxygen concentrator has a mass of less than 2.3 kg.

9. The oxygen concentrator of claim 6 wherein the oxygen concentrator has a mass of less than 1.4 kg.

10. The oxygen concentrator of claim 6 further comprising:
a rechargeable power source for actuating the control valve, motor, and ECM.

11. The oxygen concentrator of claim 6 wherein the adsorbent material comprises a zeolite which preferentially adsorbs nitrogen.

12. The oxygen concentrator of claim 6 wherein the control valve comprises a rotary valve.

13. The oxygen concentrator of claim further comprising an oxygen conserver connected to the oxygen reservoir.

14. An oxygen concentrator comprising:
an oxygen gas separator for producing oxygen-rich product gas from air by a vacuum swing adsorption (VSA) process, the process running between approximately 0.1 atm and 1.0 atm;

a reservoir for storing product gas from the separator;

a delivery system for delivering product gas from the reservoir to a patient;

a pressure sensor for providing a reservoir pressure signal as a function of product gas pressure in the reservoir;

a motor configured to drive the separator; and a control for controlling a rate of production of product gas by the separator as a function of product gas delivered from the reservoir by adjusting the speed of the motor.

15. The oxygen concentrator of claim 14 further comprising:
an oxygen conserver connected to the reservoir.

16. The oxygen concentrator of claim 14 wherein the oxygen gas separator utilizes vacuum swing adsorption to produce the oxygen-rich product gas.

17. The oxygen concentrator of claim 14 wherein the oxygen concentrator has a volume of less than 1.0 liter.

18. The oxygen concentrator of claim 14 wherein the oxygen concentrator has a mass of less then 2.3 kg.

19. The oxygen concentrator of claim 14 wherein the oxygen concentrator has a mass of less then 1.4 kg.

20. The oxygen concentrator of claim 14 wherein the oxygen gas separator comprises a plurality of gas separation columns, each column including a first filter, a bed of adsorbent material, and a second filter encased within the column.

21. The oxygen concentrator of claim 20 wherein the bed of adsorbent material comprises a zeolite that preferentially adsorbs nitrogen.

* * * * *